(12) United States Patent
Fouser et al.

(10) Patent No.: US 7,176,180 B2
(45) Date of Patent: Feb. 13, 2007

(54) TYPE 2 CYTOKINE RECEPTOR AND NUCLEIC ACIDS ENCODING SAME

(75) Inventors: Lynette Fouser, Acton, MA (US); Wei Liu, Auburndale, MA (US); Bijia Deng, Allston, MA (US)

(73) Assignee: Wyeth, Madison, NJ (US)

( * ) Notice: Subject to any disclaimer, the term of this patent is extended or adjusted under 35 U.S.C. 154(b) by 546 days.

(21) Appl. No.: 10/047,264

(22) Filed: Jan. 14, 2002

(65) Prior Publication Data

US 2003/0170839 A1 Sep. 11, 2003

Related U.S. Application Data

(60) Provisional application No. 60/270,835, filed on Feb. 23, 2001, provisional application No. 60/267,021, filed on Feb. 6, 2001, provisional application No. 60/261,442, filed on Jan. 12, 2001.

(51) Int. Cl.
*A61K 38/00* (2006.01)

(52) U.S. Cl. .................... 514/2; 530/350; 530/351; 435/69.7

(58) Field of Classification Search .............. 514/2; 530/350; 435/69.7, 6
See application file for complete search history.

(56) References Cited

U.S. PATENT DOCUMENTS

| | | | |
|---|---|---|---|
| 5,319,071 A | | 6/1994 | Dower et al. |
| 6,740,520 B2 * | | 5/2004 | Goddard et al. ............ 435/325 |
| 6,875,845 B2 | | 4/2005 | Presnell et al. |
| 6,897,292 B2 | | 5/2005 | Presnell et al. |
| 2003/0022827 A1 | | 1/2003 | Weiss et al. |
| 2003/0219862 A1* | | 11/2003 | Agarwal et al. ............ 435/69.1 |

FOREIGN PATENT DOCUMENTS

| | | |
|---|---|---|
| EP | 1 191 035 | 3/2002 |
| WO | WO 01/36467 | 5/2001 |
| WO | WO 01/40467 | 6/2001 |
| WO | WO 01/46422 | 6/2001 |
| WO | WO 01/66740 | 9/2001 |
| WO | WO 01/98342 | 12/2001 |
| WO | WO 02/12345 | 2/2002 |
| WO | WO 02/24888 | 3/2002 |
| WO | WO 02/24912 | 3/2002 |
| WO | WO 02/070655 | 9/2002 |

OTHER PUBLICATIONS

Dumoutier, et al. (2001). J Immun 166(12): 7090-7095.
Gruenberg, et al. (2001). Gen Immun 2(6): 329-334.
Kotenko and Pestka (2000). Oncogene 19: 2557-2565.
Kotenko, et al. (2001). J Immun 166(12): 7096-7103.
Xu, et al. (2001). Proc Natl Acad Sci USA 98(17): 9511-9516.

* cited by examiner

*Primary Examiner*—Gary B. Nickol
*Assistant Examiner*—Dong Jiang
(74) *Attorney, Agent, or Firm*—Finnegan, Henderson, Farabow, Garrett & Dunner, LLP

(57) ABSTRACT

The present invention provides novel isolated CRF2-12 polynucleotides and polypeptides encoded by the CRF2-12 polynucleotides. Also provided are the antibodies that immunospecifically bind to a CRF2-12 polypeptide or any derivative (including fusion derivative), variant, mutant or fragment of the CRF2-12 polypeptide, polynucleotide or antibody. The invention additionally provides methods in which the CRF2-12 polypeptide, polynucleotide and antibody are utilized in the detection and treatment of a broad range of pathological states, as well as to other uses.

11 Claims, No Drawings

SEQUENCE LISTING

<160> NUMBER OF SEQ ID NOS: 39

<210> SEQ ID NO 1
<211> LENGTH: 696
<212> TYPE: DNA
<213> ORGANISM: Human

<400> SEQUENCE: 1

```
atgatgccta acattgctt  tctaggcttc ctcatcagtt tcttccttac tggtgtagca      60
ggaactcagt caacgcatga gtctctgaag cctcagaggg tacaatttca gtcccgaaat     120
tttcacaaca ttttgcaatg gcagcctggg agggcactta ctggcaacag cagtgtctat     180
tttgtgcagt acaaaatata tggacagaga caatggaaaa ataaagaaga ctgttggggt     240
actcaagaac tctcttgtga ccttaccagt gaaacctcag acatacagga accttattac     300
ggagggtga  gggcggcctc ggctgggagc tactcagaat ggagcatgac gccgcggttc     360
actccctggt gggaaacaaa aatagatcct ccagtcatga atataaccca gtcaatggc      420
tctttgttgg taattctcca tgctccaaat ttaccatata gataccaaaa ggaaaaaaat     480
gtatctatag aagattacta tgaactacta taccgagttt ttataattaa caattcacta     540
gaaaaggagc aaaaggttta tgaagggggct cacagagcgg ttgaaattga agctctaaca     600
ccacactcca gctactgtgt agtggctgaa atatatcagc ccatgttaga cagaagaagt     660
cagagaagtg aagagagatg tgtggaaatt ccatga                                696
```

<210> SEQ ID NO 2
<211> LENGTH: 231
<212> TYPE: PRT
<213> ORGANISM: human

<400> SEQUENCE: 2

```
Met Met Pro Lys His Cys Phe Leu Gly Phe Leu Ile Ser Phe Phe Leu
 1               5                   10                  15

Thr Gly Val Ala Gly Thr Gln Ser Thr His Glu Ser Leu Lys Pro Gln
            20                  25                  30

Arg Val Gln Phe Gln Ser Arg Asn Phe His Asn Ile Leu Gln Trp Gln
        35                  40                  45

Pro Gly Arg Ala Leu Thr Gly Asn Ser Ser Val Tyr Phe Val Gln Tyr
    50                  55                  60

Lys Ile Tyr Gly Gln Arg Gln Trp Lys Asn Lys Glu Asp Cys Trp Gly
65                  70                  75                  80

Thr Gln Glu Leu Ser Cys Asp Leu Thr Ser Glu Thr Ser Asp Ile Gln
                85                  90                  95

Glu Pro Tyr Tyr Gly Arg Val Arg Ala Ala Ser Ala Gly Ser Tyr Ser
            100                 105                 110

Glu Trp Ser Met Thr Pro Arg Phe Thr Pro Trp Trp Glu Thr Lys Ile
        115                 120                 125

Asp Pro Pro Val Met Asn Ile Thr Gln Val Asn Gly Ser Leu Leu Val
    130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
                165                 170                 175

Asn Asn Ser Leu Glu Lys Glu Gln Lys Val Tyr Glu Gly Ala His Arg
            180                 185                 190
```

```
Ala Val Glu Ile Glu Ala Leu Thr Pro His Ser Ser Tyr Cys Val Val
        195                 200                 205
Ala Glu Ile Tyr Gln Pro Met Leu Asp Arg Arg Ser Gln Arg Ser Glu
    210                 215                 220
Glu Arg Cys Val Glu Ile Pro
225                 230

<210> SEQ ID NO 3
<211> LENGTH: 792
<212> TYPE: DNA
<213> ORGANISM: human

<400> SEQUENCE: 3
atgatgccta acattgctt tctaggcttc ctcatcagtt tcttccttac tggtgtagca      60
ggaactcagt caacgcatga gtctctgaag cctcagaggg tacaatttca gtcccgaaat    120
tttcacaaca ttttgcaatg gcagcctggg agggcactta ctggcaacag cagtgtctat    180
tttgtgcagt acaaaatcat gttctcatgc agcatgaaaa gctctcacca aagccaagt    240
ggatgctggc agcacatttc ttgtaacttc ccaggctgca gaacattggc taaatatgga    300
cagagacaat ggaaaaataa agaagactgt tggggtactc aagaactctc ttgtgacctt    360
accagtgaaa cctcagacat acaggaacct tattacggga gggtgagggc ggcctcggct    420
gggagctact cagaatggag catgacgccg cggttcactc cctggtggga acaaaaata    480
gatcctccag tcatgaatat aacccaagtc aatggctctt tgttggtaat tctccatgct    540
ccaaatttac catatagata ccaaaaggaa aaaatgtat ctatagaaga ttactatgaa    600
ctactatacc gagtttttat aattaacaat tcactagaaa aggagcaaaa ggtttatgaa    660
ggggctcaca gagcggttga aattgaagct ctaacaccac actccagcta ctgtgtagtg    720
gctgaaatat atcagcccat gttagacaga agaagtcaga gaagtgaaga gagatgtgtg    780
gaaattccat ga                                                        792

<210> SEQ ID NO 4
<211> LENGTH: 263
<212> TYPE: PRT
<213> ORGANISM: human

<400> SEQUENCE: 4

Met Met Pro Lys His Cys Phe Leu Gly Phe Leu Ile Ser Phe Phe Leu
1               5                   10                  15
Thr Gly Val Ala Gly Thr Gln Ser Thr His Glu Ser Leu Lys Pro Gln
            20                  25                  30
Arg Val Gln Phe Gln Ser Arg Asn Phe His Asn Ile Leu Gln Trp Gln
        35                  40                  45
Pro Gly Arg Ala Leu Thr Gly Asn Ser Ser Val Tyr Phe Val Gln Tyr
    50                  55                  60
Lys Ile Met Phe Ser Cys Ser Met Lys Ser Ser His Gln Lys Pro Ser
65                  70                  75                  80
Gly Cys Trp Gln His Ile Ser Cys Asn Phe Pro Gly Cys Arg Thr Leu
                85                  90                  95
Ala Lys Tyr Gly Gln Arg Gln Trp Lys Asn Lys Glu Asp Cys Trp Gly
            100                 105                 110
Thr Gln Glu Leu Ser Cys Asp Leu Thr Ser Glu Thr Ser Asp Ile Gln
        115                 120                 125
Glu Pro Tyr Tyr Gly Arg Val Arg Ala Ala Ser Ala Gly Ser Tyr Ser
```

-continued

```
           130                 135                 140
Glu Trp Ser Met Thr Pro Arg Phe Thr Pro Trp Trp Glu Thr Lys Ile
145                 150                 155                 160

Asp Pro Pro Val Met Asn Ile Thr Gln Val Asn Gly Ser Leu Leu Val
                165                 170                 175

Ile Leu His Ala Pro Asn Leu Pro Tyr Arg Tyr Gln Lys Glu Lys Asn
            180                 185                 190

Val Ser Ile Glu Asp Tyr Tyr Glu Leu Leu Tyr Arg Val Phe Ile Ile
        195                 200                 205

Asn Asn Ser Leu Glu Lys Glu Gln Lys Val Tyr Glu Gly Ala His Arg
    210                 215                 220

Ala Val Glu Ile Glu Ala Leu Thr Pro His Ser Ser Tyr Cys Val Val
225                 230                 235                 240

Ala Glu Ile Tyr Gln Pro Met Leu Asp Arg Arg Ser Gln Arg Ser Glu
                245                 250                 255

Glu Arg Cys Val Glu Ile Pro
            260
```

<210> SEQ ID NO 5
<211> LENGTH: 393
<212> TYPE: DNA
<213> ORGANISM: human

<400> SEQUENCE: 5

```
atgatgccta acattgctt  tctaggcttc  ctcatcagtt  tcttccttac  tggtgtagca    60
ggaactcagt caacgcatga gtctctgaag cctcagaggg tacaatttca gtcccgaaat   120
tttcacaaca ttttgcaatg gcagcctggg agggcactta ctggcaacag cagtgtctat   180
tttgtgcagt acaaaatata tggacagaga caatggaaaa ataagaaga ctgttggggt    240
actcaagaac tctcttgtga ccttaccagt gaaacctcag acatacagga accttattac   300
gggagggtga gggcggcctc ggctgggagc tactcagaat ggagcatgac gccgcggttc   360
actccctggt gggaaagagc aaaaggttta tga                                393
```

<210> SEQ ID NO 6
<211> LENGTH: 130
<212> TYPE: PRT
<213> ORGANISM: human

<400> SEQUENCE: 6

```
Met Met Pro Lys His Cys Phe Leu Gly Phe Leu Ile Ser Phe Phe Leu
1               5                   10                  15

Thr Gly Val Ala Gly Thr Gln Ser Thr His Glu Ser Leu Lys Pro Gln
            20                  25                  30

Arg Val Gln Phe Gln Ser Arg Asn Phe His Asn Ile Leu Gln Trp Gln
        35                  40                  45

Pro Gly Arg Ala Leu Thr Gly Asn Ser Ser Val Tyr Phe Val Gln Tyr
    50                  55                  60

Lys Ile Tyr Gly Gln Arg Gln Trp Lys Asn Lys Glu Asp Cys Trp Gly
65                  70                  75                  80

Thr Gln Glu Leu Ser Cys Asp Leu Thr Ser Glu Thr Ser Asp Ile Gln
                85                  90                  95

Glu Pro Tyr Tyr Gly Arg Val Arg Ala Ala Ser Ala Gly Ser Tyr Ser
            100                 105                 110

Glu Trp Ser Met Thr Pro Arg Phe Thr Pro Trp Trp Glu Arg Ala Lys
        115                 120                 125
```

Gly Leu
    130

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: PCR Primer

<400> SEQUENCE: 7
tcatggaatt tccacacatc tctcttcac                                        29

<210> SEQ ID NO 8
<211> LENGTH: 341
<212> TYPE: PRT
<213> ORGANISM: human

<400> SEQUENCE: 8

Met Ala Ala Leu Arg Gly Ala Leu Trp Gly Cys Leu Leu Cys
 1               5                  10                  15

Val Ser Gly Ile Val Pro Lys Pro Arg Asn Ala Arg Ile Ser Ser Val
            20                  25                  30

Asn Phe Arg Ser Val Leu Leu Trp Asp Pro Pro Gly Val Arg Lys Gly
        35                  40                  45

Asn Leu Ser Tyr Thr Val Gln Ala Lys Ser Ile Phe Pro Lys Gln Asn
    50                  55                  60

Phe Asn Asn Val Thr Thr Asn Leu Asn Val Thr Glu Cys Asp Val Ser
65                  70                  75                  80

Ser Leu Ser Val Tyr Gly Ala Tyr Val Leu Arg Val Arg Thr Glu Trp
                85                  90                  95

Glu Asp Glu His Ser Asp Trp Ala Val Val Arg Phe Lys Pro Met Ala
            100                 105                 110

Asp Thr Val Ile Gly Pro Pro Ser Val Asn Val Lys Ser Glu Ser Gly
        115                 120                 125

Thr Leu His Val Asp Phe Thr Gly Pro Ala Ala Asp Arg Glu His Asp
    130                 135                 140

Lys Trp Ser Leu Lys Gln Tyr Tyr Gly Ser Trp Ile Tyr Arg Ile Leu
145                 150                 155                 160

Tyr Trp Lys Lys Gly Ser Asn Lys Lys Val Ile His Ile Asp Thr Lys
                165                 170                 175

His Asn Ser Glu Ile Leu Ser Gln Leu Glu Pro Trp Thr Ile Tyr Cys
            180                 185                 190

Ile Gln Val Gln Gly Val Ile Pro Glu Trp Asn Lys Thr Gly Glu Arg
        195                 200                 205

Ser Gln Glu Leu Cys Glu Gln Thr Thr His Asn Gly Val Thr Pro Val
    210                 215                 220

Trp Ile Val Val Thr Val Leu Leu Gly Ser Met Leu Ala Val Ile Ile
225                 230                 235                 240

Ser Val Pro Val Cys Phe Phe Ala Phe Trp Tyr Leu Tyr Arg Phe Thr
                245                 250                 255

Lys His Val Phe Phe Pro Ser Tyr Ile Phe Pro Gln His Leu Lys Glu
            260                 265                 270

Phe Phe Ser Pro Val Pro Gln Glu Glu His His Phe His Asp Trp Leu
        275                 280                 285

Thr Val Ile Ser Glu Glu Pro Lys Ser Gln Arg Asp Glu Thr Val Glu

```
            290               295               300
Glu Ala Ser Arg Thr Ala Glu His His Gln Asp Ser Lys Gln Glu Ile
305                 310                 315                 320

Ser Asp Ser Glu Ile Leu Pro Pro Leu Glu Arg Asp Gln Thr Leu Leu
                325                 330                 335

Thr Leu Gln Ser Gly
            340

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: PCR Primer

<400> SEQUENCE: 9
atgatgccta aacattgctt tctagg                                         26

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence:PCR Primer

<400> SEQUENCE: 10
tcatggaatt tccacacatc tctcttcac                                      29

<210> SEQ ID NO 11
<211> LENGTH: 728
<212> TYPE: DNA
<213> ORGANISM: human

<400> SEQUENCE: 11
ggaactctgg ttgccagaca agcacacttg caaccatgat gcctaagcat tgccttctag    60
gtctcctcat catactcttg agcagtgcaa cagaaataca accagctcgt gtatctctga   120
cgccccagaa ggtccgattt cagtccagaa atttccacaa tattttgcac tggcaagcag   180
ggagctctct ccccagcaac aacagcatct actttgtgca gtacaagatg tatggacaga   240
gccaatggga agataaagtt gactgctggg ggaccacggc gctcttctgt gacctgacca   300
atgaaacctt agacccatac gagctgtatt acgggagggt gatgacggcc tgtgctggac   360
gccactctgc ctggaccagg acaccccgct tcactccatg gtgggaaaca aaactagatc   420
ctccggtcgt gactataacc cgagttaacg catctttgcg ggtgcttctc cgtcctccag   480
agttgccaaa tagaaaccaa agtggaaaaa atgcatccat ggaaacttac tacggcttag   540
tatacagagt tttcacaatc aacaattcac tagagaagga gcaaaaagcc tatgaaggga   600
ctcagagagc tgttgaaatt gaaggtctga tacctcattc cagctactgc gtagtggctg   660
aaatgtacca gcccatgttt gacagaagaa gcccaagaag caaggagaga tgtgtgcaga   720
ttccatga                                                            728

<210> SEQ ID NO 12
<211> LENGTH: 230
<212> TYPE: PRT
<213> ORGANISM: human

<400> SEQUENCE: 12

Met Met Pro Lys His Cys Leu Leu Gly Leu Leu Ile Ile Leu Leu Ser
  1               5                  10                  15
```

-continued

```
Ser Ala Thr Glu Ile Gln Pro Ala Arg Val Ser Leu Thr Pro Gln Lys
         20                  25                  30

Val Arg Phe Gln Ser Arg Asn Phe His Asn Ile Leu His Trp Gln Ala
         35                  40                  45

Gly Ser Ser Leu Pro Ser Asn Asn Ser Ile Tyr Phe Val Gln Tyr Lys
         50                  55                  60

Met Tyr Gly Gln Ser Gln Trp Glu Asp Lys Val Asp Cys Trp Gly Thr
 65                  70                  75                  80

Thr Ala Leu Phe Cys Asp Leu Thr Asn Glu Thr Leu Asp Pro Tyr Glu
                 85                  90                  95

Leu Tyr Tyr Gly Arg Val Met Thr Ala Cys Ala Gly Arg His Ser Ala
                100                 105                 110

Trp Thr Arg Thr Pro Arg Phe Thr Pro Trp Trp Glu Thr Lys Leu Asp
                115                 120                 125

Pro Pro Val Val Thr Ile Thr Arg Val Asn Ala Ser Leu Arg Val Leu
        130                 135                 140

Leu Arg Pro Pro Glu Leu Pro Asn Arg Asn Gln Ser Gly Lys Asn Ala
145                 150                 155                 160

Ser Met Glu Thr Tyr Tyr Gly Leu Val Tyr Arg Val Phe Thr Ile Asn
                165                 170                 175

Asn Ser Leu Glu Lys Glu Gln Lys Ala Tyr Glu Gly Thr Gln Arg Ala
                180                 185                 190

Val Glu Ile Glu Gly Leu Ile Pro His Ser Ser Tyr Cys Val Val Ala
                195                 200                 205

Glu Met Tyr Gln Pro Met Phe Asp Arg Arg Ser Pro Arg Ser Lys Glu
        210                 215                 220

Arg Cys Val Gln Ile Pro
225                 230

<210> SEQ ID NO 13
<211> LENGTH: 12
<212> TYPE: PRT
<213> ORGANISM: human
<220> FEATURE:
<221> NAME/KEY: VARIANT
<222> LOCATION: (7)
<223> OTHER INFORMATION: Wherein X is the amino acid L or F
<220> FEATURE:
<221> NAME/KEY: VARIANT
<222> LOCATION: (10)
<223> OTHER INFORMATION: Wherein X is the amino acid L or F

<400> SEQUENCE: 13

Met Met Pro Lys His Cys Xaa Leu Gly Xaa Leu Ile
 1               5                  10

<210> SEQ ID NO 14
<211> LENGTH: 15
<212> TYPE: PRT
<213> ORGANISM: human
<220> FEATURE:
<221> NAME/KEY: VARIANT
<222> LOCATION: (11)
<223> OTHER INFORMATION: Wherein X is the amino acid H or Q
<220> FEATURE:
<221> NAME/KEY: VARIANT
<222> LOCATION: (14)
<223> OTHER INFORMATION: Wherein X is the amino acid A or P

<400> SEQUENCE: 14

Phe Gln Ser Arg Asn Phe His Asn Ile Leu Xaa Trp Gln Xaa Gly
```

```
<210> SEQ ID NO 15
<211> LENGTH: 15
<212> TYPE: PRT
<213> ORGANISM: human
<220> FEATURE:
<221> NAME/KEY: VARIANT
<222> LOCATION: (2)
<223> OTHER INFORMATION: Wherein X is the amino acid I or V
<220> FEATURE:
<221> NAME/KEY: VARIANT
<222> LOCATION: (9)
<223> OTHER INFORMATION: Wherein X is the amino acid M or I
<220> FEATURE:
<221> NAME/KEY: VARIANT
<222> LOCATION: (13)
<223> OTHER INFORMATION: Wherein X is the amino acid S or R

<400> SEQUENCE: 15

Ser Xaa Tyr Phe Val Gln Tyr Lys Xaa Tyr Gly Gln Xaa Gln Trp
 1               5                  10                  15

<210> SEQ ID NO 16
<211> LENGTH: 16
<212> TYPE: PRT
<213> ORGANISM: human
<220> FEATURE:
<221> NAME/KEY: VARIANT
<222> LOCATION: (12)
<223> OTHER INFORMATION: wherein X is the amino acid L or I

<400> SEQUENCE: 16

Thr Pro Arg Phe Thr Pro Trp Trp Glu Thr Lys Xaa Asp Pro Pro Val
 1               5                  10                  15

<210> SEQ ID NO 17
<211> LENGTH: 21
<212> TYPE: PRT
<213> ORGANISM: human
<220> FEATURE:
<221> NAME/KEY: VARIANT
<222> LOCATION: (2)
<223> OTHER INFORMATION: Wherein X is the amino acid V or L
<220> FEATURE:
<221> NAME/KEY: VARIANT
<222> LOCATION: (7)
<223> OTHER INFORMATION: Wherein X is the amono acid T or I
<220> FEATURE:
<221> NAME/KEY: VARIANT
<222> LOCATION: (18)
<223> OTHER INFORMATION: Wherein X is the amino acid A or V

<400> SEQUENCE: 17

Leu Xaa Tyr Arg Val Phe Xaa Ile Asn Asn Ser Leu Glu Lys Glu Gln
 1               5                  10                  15

Lys Xaa Tyr Glu Gly
            20

<210> SEQ ID NO 18
<211> LENGTH: 24
<212> TYPE: PRT
<213> ORGANISM: human
<220> FEATURE:
<221> NAME/KEY: VARIANT
<222> LOCATION: (7)
<223> OTHER INFORMATION: Wherein X is the amino acid G or A
<220> FEATURE:
<221> NAME/KEY: VARIANT
<222> LOCATION: (9)
<223> OTHER INFORMATION: Wherein X is the amino acid I or T
```

```
-continued

<220> FEATURE:
<221> NAME/KEY: VARIANT
<222> LOCATION: (20)
<223> OTHER INFORMATION: Wherein X is the amino acid M or I

<400> SEQUENCE: 18

Arg Ala Val Glu Ile Glu Xaa Leu Xaa Pro His Ser Ser Tyr Cys Val
  1               5                  10                  15

Val Ala Glu Xaa Tyr Gln Pro Met
             20

<210> SEQ ID NO 19
<211> LENGTH: 15
<212> TYPE: PRT
<213> ORGANISM: human
<220> FEATURE:
<221> NAME/KEY: VARIANT
<222> LOCATION: (5)
<223> OTHER INFORMATION: Wherein X is the amino acid P or Q
<220> FEATURE:
<221> NAME/KEY: VARIANT
<222> LOCATION: (8)
<223> OTHER INFORMATION: Wherein X is the amino acid K or E
<220> FEATURE:
<221> NAME/KEY: VARIANT
<222> LOCATION: (13)
<223> OTHER INFORMATION: Wherein X is the amino acid Q or E

<400> SEQUENCE: 19

Asp Arg Arg Ser Xaa Arg Ser Xaa Glu Arg Cys Val Xaa Ile Pro
  1               5                  10                  15

<210> SEQ ID NO 20
<211> LENGTH: 231
<212> TYPE: PRT
<213> ORGANISM: human

<400> SEQUENCE: 20

Met Met Pro Lys His Cys Phe Leu Gly Phe Leu Ile Ser Phe Phe Leu
  1               5                  10                  15

Thr Gly Val Ala Gly Thr Asn Ser Thr His Glu Ser Leu Lys Pro Gln
             20                  25                  30

Arg Val Gln Phe Gln Ser Arg Asn Phe His Asn Ile Leu Gln Trp Gln
         35                  40                  45

Pro Gly Arg Ala Leu Thr Gly Asn Ser Ser Val Tyr Phe Val Gln Tyr
     50                  55                  60

Lys Ile Tyr Gly Gln Arg Gln Trp Lys Asn Lys Glu Asp Cys Trp Gly
 65                  70                  75                  80

Thr Gln Glu Leu Ser Cys Asp Leu Thr Ser Glu Thr Ser Asp Ile Gln
                 85                  90                  95

Glu Pro Tyr Tyr Gly Arg Val Arg Ala Ala Ser Ala Gly Ser Tyr Ser
            100                 105                 110

Glu Trp Ser Met Thr Pro Arg Phe Thr Pro Trp Trp Glu Thr Lys Ile
        115                 120                 125

Asp Pro Pro Val Met Asn Ile Thr Gln Val Asn Gly Ser Leu Leu Val
    130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
                165                 170                 175

Asn Asn Ser Leu Glu Lys Glu Gln Lys Val Tyr Glu Gly Ala His Arg
            180                 185                 190
```

```
Ala Val Glu Ile Glu Ala Leu Thr Pro His Ser Ser Tyr Cys Val Val
            195                 200                 205

Ala Glu Ile Tyr Gln Pro Met Leu Asp Arg Arg Ser Gln Arg Ser Glu
    210                 215                 220

Glu Arg Cys Val Glu Ile Pro
225                 230
```

<210> SEQ ID NO 21
<211> LENGTH: 231
<212> TYPE: PRT
<213> ORGANISM: human

<400> SEQUENCE: 21

```
Met Met Pro Lys His Cys Phe Leu Gly Phe Leu Ile Ser Phe Phe Leu
1               5                   10                  15

Thr Gly Val Ala Gly Thr Gln Ser Thr Arg Glu Ser Leu Lys Pro Gln
            20                  25                  30

Arg Val Gln Phe Gln Ser Arg Asn Phe His Asn Ile Leu Gln Trp Gln
        35                  40                  45

Pro Gly Arg Ala Leu Thr Gly Asn Ser Ser Val Tyr Phe Val Gln Tyr
    50                  55                  60

Lys Ile Tyr Gly Gln Arg Gln Trp Lys Asn Lys Glu Asp Cys Trp Gly
65                  70                  75                  80

Thr Gln Glu Leu Ser Cys Asp Leu Thr Ser Glu Thr Ser Asp Ile Gln
                85                  90                  95

Glu Pro Tyr Tyr Gly Arg Val Arg Ala Ala Ser Ala Gly Ser Tyr Ser
            100                 105                 110

Glu Trp Ser Met Thr Pro Arg Phe Thr Pro Trp Trp Glu Thr Lys Ile
        115                 120                 125

Asp Pro Pro Val Met Asn Ile Thr Gln Val Asn Gly Ser Leu Leu Val
130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
                165                 170                 175

Asn Asn Ser Leu Glu Lys Glu Gln Lys Val Tyr Glu Gly Ala His Arg
            180                 185                 190

Ala Val Glu Ile Glu Ala Leu Thr Pro His Ser Ser Tyr Cys Val Val
        195                 200                 205

Ala Glu Ile Tyr Gln Pro Met Leu Asp Arg Arg Ser Gln Arg Ser Glu
    210                 215                 220

Glu Arg Cys Val Glu Ile Pro
225                 230
```

<210> SEQ ID NO 22
<211> LENGTH: 231
<212> TYPE: PRT
<213> ORGANISM: human

<400> SEQUENCE: 22

```
Met Met Pro Lys His Cys Phe Leu Gly Phe Leu Ile Ser Phe Phe Leu
1               5                   10                  15

Thr Gly Val Ala Gly Thr Gln Ser Thr His Asp Ser Leu Lys Pro Gln
            20                  25                  30

Arg Val Gln Phe Gln Ser Arg Asn Phe His Asn Ile Leu Gln Trp Gln
        35                  40                  45
```

```
Pro Gly Arg Ala Leu Thr Gly Asn Ser Ser Val Tyr Phe Val Gln Tyr
    50                  55                  60

Lys Ile Tyr Gly Gln Arg Gln Trp Lys Asn Lys Glu Asp Cys Trp Gly
 65                  70                  75                  80

Thr Gln Glu Leu Ser Cys Asp Leu Thr Ser Glu Thr Ser Asp Ile Gln
                 85                  90                  95

Glu Pro Tyr Tyr Gly Arg Val Arg Ala Ala Ser Ala Gly Ser Tyr Ser
                100                 105                 110

Glu Trp Ser Met Thr Pro Arg Phe Thr Pro Trp Trp Glu Thr Lys Ile
            115                 120                 125

Asp Pro Pro Val Met Asn Ile Thr Gln Val Asn Gly Ser Leu Leu Val
    130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
                165                 170                 175

Asn Asn Ser Leu Glu Lys Glu Gln Lys Val Tyr Glu Gly Ala His Arg
            180                 185                 190

Ala Val Glu Ile Glu Ala Leu Thr Pro His Ser Ser Tyr Cys Val Val
        195                 200                 205

Ala Glu Ile Tyr Gln Pro Met Leu Asp Arg Arg Ser Gln Arg Ser Glu
    210                 215                 220

Glu Arg Cys Val Glu Ile Pro
225                 230

<210> SEQ ID NO 23
<211> LENGTH: 231
<212> TYPE: PRT
<213> ORGANISM: human

<400> SEQUENCE: 23

Met Met Pro Lys His Cys Phe Leu Gly Phe Leu Ile Ser Phe Phe Leu
  1               5                  10                  15

Thr Gly Val Ala Gly Thr Gln Ser Thr His Glu Ser Val Lys Pro Gln
             20                  25                  30

Arg Val Gln Phe Gln Ser Arg Asn Phe His Asn Ile Leu Gln Trp Gln
         35                  40                  45

Pro Gly Arg Ala Leu Thr Gly Asn Ser Ser Val Tyr Phe Val Gln Tyr
    50                  55                  60

Lys Ile Tyr Gly Gln Arg Gln Trp Lys Asn Lys Glu Asp Cys Trp Gly
 65                  70                  75                  80

Thr Gln Glu Leu Ser Cys Asp Leu Thr Ser Glu Thr Ser Asp Ile Gln
                 85                  90                  95

Glu Pro Tyr Tyr Gly Arg Val Arg Ala Ala Ser Ala Gly Ser Tyr Ser
                100                 105                 110

Glu Trp Ser Met Thr Pro Arg Phe Thr Pro Trp Trp Glu Thr Lys Ile
            115                 120                 125

Asp Pro Pro Val Met Asn Ile Thr Gln Val Asn Gly Ser Leu Leu Val
    130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
                165                 170                 175

Asn Asn Ser Leu Glu Lys Glu Gln Lys Val Tyr Glu Gly Ala His Arg
            180                 185                 190
```

-continued

```
                180                 185                 190
Ala Val Glu Ile Glu Ala Leu Thr Pro His Ser Ser Tyr Cys Val Val
            195                 200                 205

Ala Glu Ile Tyr Gln Pro Met Leu Asp Arg Arg Ser Gln Arg Ser Glu
        210                 215                 220

Glu Arg Cys Val Glu Ile Pro
225                 230

<210> SEQ ID NO 24
<211> LENGTH: 231
<212> TYPE: PRT
<213> ORGANISM: human

<400> SEQUENCE: 24

Met Met Pro Lys His Cys Phe Leu Gly Phe Leu Ile Ser Phe Phe Leu
  1               5                  10                  15

Thr Gly Val Ala Gly Thr Gln Ser Thr His Glu Ser Leu His Pro Gln
            20                  25                  30

Arg Val Gln Phe Gln Ser Arg Asn Phe His Asn Ile Leu Gln Trp Gln
        35                  40                  45

Pro Gly Arg Ala Leu Thr Gly Asn Ser Ser Val Tyr Phe Val Gln Tyr
    50                  55                  60

Lys Ile Tyr Gly Gln Arg Gln Trp Lys Asn Lys Glu Asp Cys Trp Gly
 65                  70                  75                  80

Thr Gln Glu Leu Ser Cys Asp Leu Thr Ser Glu Thr Ser Asp Ile Gln
                85                  90                  95

Glu Pro Tyr Tyr Gly Arg Val Arg Ala Ala Ser Ala Gly Ser Tyr Ser
            100                 105                 110

Glu Trp Ser Met Thr Pro Arg Phe Thr Pro Trp Trp Glu Thr Lys Ile
        115                 120                 125

Asp Pro Pro Val Met Asn Ile Thr Gln Val Asn Gly Ser Leu Leu Val
    130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
                165                 170                 175

Asn Asn Ser Leu Glu Lys Glu Gln Lys Val Tyr Glu Gly Ala His Arg
            180                 185                 190

Ala Val Glu Ile Glu Ala Leu Thr Pro His Ser Ser Tyr Cys Val Val
        195                 200                 205

Ala Glu Ile Tyr Gln Pro Met Leu Asp Arg Arg Ser Gln Arg Ser Glu
    210                 215                 220

Glu Arg Cys Val Glu Ile Pro
225                 230

<210> SEQ ID NO 25
<211> LENGTH: 231
<212> TYPE: PRT
<213> ORGANISM: human

<400> SEQUENCE: 25

Met Met Pro Lys His Cys Phe Leu Gly Phe Leu Ile Ser Phe Phe Leu
  1               5                  10                  15

Thr Gly Val Ala Gly Thr Gln Ser Thr His Glu Ser Leu Lys Pro Gln
            20                  25                  30

Lys Val Gln Phe Gln Ser Arg Asn Phe His Asn Ile Leu Gln Trp Gln
```

```
                35                  40                  45
Pro Gly Arg Ala Leu Thr Gly Asn Ser Ser Val Tyr Phe Val Gln Tyr
        50                  55                  60

Lys Ile Tyr Gly Gln Arg Gln Trp Lys Asn Lys Glu Asp Cys Trp Gly
 65                  70                  75                  80

Thr Gln Glu Leu Ser Cys Asp Leu Thr Ser Glu Thr Ser Asp Ile Gln
                85                  90                  95

Glu Pro Tyr Tyr Gly Arg Val Arg Ala Ala Ser Ala Gly Ser Tyr Ser
            100                 105                 110

Glu Trp Ser Met Thr Pro Arg Phe Thr Pro Trp Trp Glu Thr Lys Ile
            115                 120                 125

Asp Pro Pro Val Met Asn Ile Thr Gln Val Asn Gly Ser Leu Leu Val
130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
            165                 170                 175

Asn Asn Ser Leu Glu Lys Glu Gln Lys Val Tyr Glu Gly Ala His Arg
            180                 185                 190

Ala Val Glu Ile Glu Ala Leu Thr Pro His Ser Ser Tyr Cys Val Val
            195                 200                 205

Ala Glu Ile Tyr Gln Pro Met Leu Asp Arg Arg Ser Gln Arg Ser Glu
        210                 215                 220

Glu Arg Cys Val Glu Ile Pro
225                 230

<210> SEQ ID NO 26
<211> LENGTH: 231
<212> TYPE: PRT
<213> ORGANISM: human

<400> SEQUENCE: 26

Met Met Pro Lys His Cys Phe Leu Gly Phe Leu Ile Ser Phe Phe Leu
  1               5                  10                  15

Thr Gly Val Ala Gly Thr Gln Ser Thr His Glu Ser Leu Lys Pro Gln
            20                  25                  30

Arg Val Gln Phe Gln Ser Arg Gln Phe His Asn Ile Leu Gln Trp Gln
            35                  40                  45

Pro Gly Arg Ala Leu Thr Gly Asn Ser Ser Val Tyr Phe Val Gln Tyr
        50                  55                  60

Lys Ile Tyr Gly Gln Arg Gln Trp Lys Asn Lys Glu Asp Cys Trp Gly
 65                  70                  75                  80

Thr Gln Glu Leu Ser Cys Asp Leu Thr Ser Glu Thr Ser Asp Ile Gln
                85                  90                  95

Glu Pro Tyr Tyr Gly Arg Val Arg Ala Ala Ser Ala Gly Ser Tyr Ser
            100                 105                 110

Glu Trp Ser Met Thr Pro Arg Phe Thr Pro Trp Trp Glu Thr Lys Ile
            115                 120                 125

Asp Pro Pro Val Met Asn Ile Thr Gln Val Asn Gly Ser Leu Leu Val
130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
            165                 170                 175
```

```
Asn Asn Ser Leu Glu Lys Glu Gln Lys Val Tyr Glu Gly Ala His Arg
            180                 185                 190

Ala Val Glu Ile Glu Ala Leu Thr Pro His Ser Ser Tyr Cys Val Val
        195                 200                 205

Ala Glu Ile Tyr Gln Pro Met Leu Asp Arg Arg Ser Gln Arg Ser Glu
    210                 215                 220

Glu Arg Cys Val Glu Ile Pro
225                 230

<210> SEQ ID NO 27
<211> LENGTH: 231
<212> TYPE: PRT
<213> ORGANISM: human

<400> SEQUENCE: 27

Met Met Pro Lys His Cys Phe Leu Gly Phe Leu Ile Ser Phe Phe Leu
  1               5                  10                  15

Thr Gly Val Ala Gly Thr Gln Ser Thr His Glu Ser Leu Lys Pro Gln
             20                  25                  30

Arg Val Gln Phe Gln Ser Arg Asn Phe His Asn Ile Val Gln Trp Gln
         35                  40                  45

Pro Gly Arg Ala Leu Thr Gly Asn Ser Ser Val Tyr Phe Val Gln Tyr
     50                  55                  60

Lys Ile Tyr Gly Gln Arg Gln Trp Lys Asn Lys Glu Asp Cys Trp Gly
 65                  70                  75                  80

Thr Gln Glu Leu Ser Cys Asp Leu Thr Ser Glu Thr Ser Asp Ile Gln
                 85                  90                  95

Glu Pro Tyr Tyr Gly Arg Val Arg Ala Ala Ser Ala Gly Ser Tyr Ser
            100                 105                 110

Glu Trp Ser Met Thr Pro Arg Phe Thr Pro Trp Trp Glu Thr Lys Ile
        115                 120                 125

Asp Pro Pro Val Met Asn Ile Thr Gln Val Asn Gly Ser Leu Leu Val
    130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
                165                 170                 175

Asn Asn Ser Leu Glu Lys Glu Gln Lys Val Tyr Glu Gly Ala His Arg
            180                 185                 190

Ala Val Glu Ile Glu Ala Leu Thr Pro His Ser Ser Tyr Cys Val Val
        195                 200                 205

Ala Glu Ile Tyr Gln Pro Met Leu Asp Arg Arg Ser Gln Arg Ser Glu
    210                 215                 220

Glu Arg Cys Val Glu Ile Pro
225                 230

<210> SEQ ID NO 28
<211> LENGTH: 231
<212> TYPE: PRT
<213> ORGANISM: human

<400> SEQUENCE: 28

Met Met Pro Lys His Cys Phe Leu Gly Phe Leu Ile Ser Phe Phe Leu
  1               5                  10                  15

Thr Gly Val Ala Gly Thr Gln Ser Thr His Glu Ser Leu Lys Pro Gln
             20                  25                  30
```

-continued

```
Arg Val Gln Phe Gln Ser Arg Asn Phe His Asn Ile Leu Gln Trp Gln
         35                  40                  45

Pro Gly Arg Leu Leu Thr Gly Asn Ser Ser Val Tyr Phe Val Gln Tyr
     50                  55                  60

Lys Ile Tyr Gly Gln Arg Gln Trp Lys Asn Lys Glu Asp Cys Trp Gly
 65                  70                  75                  80

Thr Gln Glu Leu Ser Cys Asp Leu Thr Ser Glu Thr Ser Asp Ile Gln
                 85                  90                  95

Glu Pro Tyr Tyr Gly Arg Val Arg Ala Ala Ser Ala Gly Ser Tyr Ser
            100                 105                 110

Glu Trp Ser Met Thr Pro Arg Phe Thr Pro Trp Trp Glu Thr Lys Ile
            115                 120                 125

Asp Pro Pro Val Met Asn Ile Thr Gln Val Asn Gly Ser Leu Leu Val
    130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
                165                 170                 175

Asn Asn Ser Leu Glu Lys Glu Gln Lys Val Tyr Glu Gly Ala His Arg
            180                 185                 190

Ala Val Glu Ile Glu Ala Leu Thr Pro His Ser Ser Tyr Cys Val Val
            195                 200                 205

Ala Glu Ile Tyr Gln Pro Met Leu Asp Arg Arg Ser Gln Arg Ser Glu
    210                 215                 220

Glu Arg Cys Val Glu Ile Pro
225                 230

<210> SEQ ID NO 29
<211> LENGTH: 231
<212> TYPE: PRT
<213> ORGANISM: human

<400> SEQUENCE: 29

Met Met Pro Lys His Cys Phe Leu Gly Phe Leu Ile Ser Phe Phe Leu
 1               5                  10                  15

Thr Gly Val Ala Gly Thr Gln Ser Thr His Glu Ser Leu Lys Pro Gln
            20                  25                  30

Arg Val Gln Phe Gln Ser Arg Asn Phe His Asn Ile Leu Gln Trp Gln
         35                  40                  45

Pro Gly Arg Ala Ala Thr Gly Asn Ser Ser Val Tyr Phe Val Gln Tyr
     50                  55                  60

Lys Ile Tyr Gly Gln Arg Gln Trp Lys Asn Lys Glu Asp Cys Trp Gly
 65                  70                  75                  80

Thr Gln Glu Leu Ser Cys Asp Leu Thr Ser Glu Thr Ser Asp Ile Gln
                 85                  90                  95

Glu Pro Tyr Tyr Gly Arg Val Arg Ala Ala Ser Ala Gly Ser Tyr Ser
            100                 105                 110

Glu Trp Ser Met Thr Pro Arg Phe Thr Pro Trp Trp Glu Thr Lys Ile
            115                 120                 125

Asp Pro Pro Val Met Asn Ile Thr Gln Val Asn Gly Ser Leu Leu Val
    130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
                165                 170                 175
```

```
Asn Asn Ser Leu Glu Lys Glu Gln Lys Val Tyr Glu Gly Ala His Arg
            180                 185                 190

Ala Val Glu Ile Glu Ala Leu Thr Pro His Ser Ser Tyr Cys Val Val
            195                 200                 205

Ala Glu Ile Tyr Gln Pro Met Leu Asp Arg Arg Ser Gln Arg Ser Glu
            210                 215                 220

Glu Arg Cys Val Glu Ile Pro
225                 230

<210> SEQ ID NO 30
<211> LENGTH: 231
<212> TYPE: PRT
<213> ORGANISM: human

<400> SEQUENCE: 30

Met Met Pro Lys His Cys Phe Leu Gly Phe Leu Ile Ser Phe Phe Leu
 1               5                  10                  15

Thr Gly Val Ala Gly Thr Gln Ser Thr His Glu Ser Leu Lys Pro Gln
            20                  25                  30

Arg Val Gln Phe Gln Ser Arg Asn Phe His Asn Ile Leu Gln Trp Gln
        35                  40                  45

Pro Gly Arg Ala Leu Thr Gly Asn Ser Ser Ile Tyr Phe Val Gln Tyr
    50                  55                  60

Lys Ile Tyr Gly Gln Arg Gln Trp Lys Asn Lys Glu Asp Cys Trp Gly
65                  70                  75                  80

Thr Gln Glu Leu Ser Cys Asp Leu Thr Ser Glu Thr Ser Asp Ile Gln
                85                  90                  95

Glu Pro Tyr Tyr Gly Arg Val Arg Ala Ala Ser Ala Gly Ser Tyr Ser
            100                 105                 110

Glu Trp Ser Met Thr Pro Arg Phe Thr Pro Trp Trp Glu Thr Lys Ile
            115                 120                 125

Asp Pro Pro Val Met Asn Ile Thr Gln Val Asn Gly Ser Leu Leu Val
        130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
                165                 170                 175

Asn Asn Ser Leu Glu Lys Glu Gln Lys Val Tyr Glu Gly Ala His Arg
            180                 185                 190

Ala Val Glu Ile Glu Ala Leu Thr Pro His Ser Ser Tyr Cys Val Val
            195                 200                 205

Ala Glu Ile Tyr Gln Pro Met Leu Asp Arg Arg Ser Gln Arg Ser Glu
            210                 215                 220

Glu Arg Cys Val Glu Ile Pro
225                 230

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence:PCR Primer

<400> SEQUENCE: 31
gaattcgtcg acccaccatg cctaagcatt gccttc                              36
```

-continued

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence:PCR Primer

<400> SEQUENCE: 32
tggaatctgc acacatctct cc                                                  22

<210> SEQ ID NO 33
<211> LENGTH: 199
<212> TYPE: PRT
<213> ORGANISM: human
<220> FEATURE:
<221> NAME/KEY: VARIANT
<222> LOCATION: (139)
<223> OTHER INFORMATION: Wherein "X" is a space inserted in the Blast
      alignment analysis.

<400> SEQUENCE: 33

Lys Pro Gln Arg Val Gln Phe Gln Ser Arg Asn Phe His Asn Ile Leu
 1               5                  10                  15

Gln Trp Gln Pro Gly Arg Ala Leu Thr Gly Asn Ser Ser Val Tyr Phe
            20                  25                  30

Val Gln Tyr Lys Ile Tyr Gly Gln Arg Gln Trp Lys Asn Lys Glu Asp
        35                  40                  45

Cys Trp Gly Thr Gln Glu Leu Ser Cys Asp Leu Thr Ser Glu Thr Ser
    50                  55                  60

Asp Ile Gln Glu Pro Tyr Tyr Gly Arg Val Arg Ala Ala Ser Ala Gly
65                  70                  75                  80

Ser Tyr Ser Glu Trp Ser Met Thr Pro Arg Phe Thr Pro Trp Trp Glu
                85                  90                  95

Thr Lys Ile Asp Pro Pro Val Met Asn Ile Thr Gln Val Asn Gly Ser
            100                 105                 110

Leu Leu Val Ile Leu His Ala Pro Asn Leu Pro Tyr Arg Tyr Gln Lys
        115                 120                 125

Glu Lys Asn Val Ser Ile Glu Asp Tyr Tyr Xaa Glu Leu Leu Tyr Arg
    130                 135                 140

Val Phe Ile Ile Asn Asn Ser Leu Glu Lys Glu Gln Lys Val Tyr Glu
145                 150                 155                 160

Gly Ala His Arg Ala Val Glu Ile Glu Ala Leu Thr Pro His Ser Ser
                165                 170                 175

Tyr Cys Val Val Ala Glu Ile Tyr Gln Pro Met Leu Asp Arg Arg Ser
            180                 185                 190

Gln Arg Ser Glu Glu Arg Cys
        195

<210> SEQ ID NO 34
<211> LENGTH: 231
<212> TYPE: PRT
<213> ORGANISM: human

<400> SEQUENCE: 34

Ser Met Met Pro Lys His Cys Leu Leu Gly Leu Leu Ile Ile Leu Leu
 1               5                  10                  15

Ser Ser Ala Thr Glu Ile Gln Pro Ala Arg Val Ser Leu Thr Pro Gln
            20                  25                  30

Lys Val Arg Phe Gln Ser Arg Asn Phe His Asn Ile Leu His Trp Gln
        35                  40                  45

```
Ala Gly Ser Ser Leu Pro Ser Asn Asn Ser Ile Tyr Phe Val Gln Tyr
     50                  55                  60

Lys Met Tyr Gly Gln Ser Gln Trp Glu Asp Lys Val Asp Cys Trp Gly
 65                  70                  75                  80

Thr Thr Ala Leu Phe Cys Asp Leu Thr Asn Glu Thr Leu Asp Pro Tyr
                 85                  90                  95

Glu Leu Tyr Tyr Gly Arg Val Met Thr Ala Cys Ala Gly Arg His Ser
             100                 105                 110

Ala Trp Thr Arg Thr Pro Arg Phe Thr Pro Trp Trp Glu Thr Lys Leu
         115                 120                 125

Asp Pro Pro Val Val Thr Ile Thr Arg Val Asn Ala Ser Leu Arg Val
     130                 135                 140

Leu Leu Arg Pro Pro Glu Leu Pro Asn Arg Asn Gln Ser Gly Lys Asn
145                 150                 155                 160

Ala Ser Met Glu Thr Tyr Tyr Gly Leu Val Tyr Arg Val Phe Thr Ile
                165                 170                 175

Asn Asn Ser Leu Glu Lys Glu Gln Lys Ala Tyr Glu Gly Thr Gln Arg
            180                 185                 190

Ala Val Glu Ile Glu Gly Leu Ile Pro His Ser Ser Tyr Cys Val Val
        195                 200                 205

Ala Glu Met Tyr Gln Pro Met Phe Asp Arg Arg Ser Pro Arg Ser Lys
    210                 215                 220

Glu Arg Cys Val Gln Ile Pro
225                 230

<210> SEQ ID NO 35
<211> LENGTH: 231
<212> TYPE: PRT
<213> ORGANISM: human

<400> SEQUENCE: 35

Met Met Pro Lys His Cys Phe Leu Gly Phe Leu Ile Ser Phe Phe Leu
  1               5                  10                  15

Thr Gly Val Ala Gly Thr Gln Ser Thr His Glu Ser Leu Lys Pro Gln
             20                  25                  30

Arg Val Gln Phe Gln Ser Arg Asn Phe His Asn Ile Leu Gln Trp Gln
         35                  40                  45

Pro Gly Arg Ala Leu Thr Gly Asn Ser Ser Val Tyr Phe Val Gln Tyr
     50                  55                  60

Lys Ile Tyr Gly Gln Arg Gln Trp Lys Asn Lys Glu Asp Cys Trp Gly
 65                  70                  75                  80

Thr Gln Glu Leu Ser Cys Asp Leu Thr Ser Glu Thr Ser Asp Ile Gln
                 85                  90                  95

Glu Pro Tyr Tyr Gly Arg Val Arg Ala Ala Ser Ala Gly Ser Tyr Ser
             100                 105                 110

Glu Trp Ser Met Thr Pro Arg Phe Thr Pro Trp Trp Glu Thr Lys Ile
         115                 120                 125

Asp Pro Pro Val Met Asn Ile Thr Gln Val Asn Gly Ser Leu Leu Val
     130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
                165                 170                 175

Asn Asn Ser Leu Glu Lys Glu Gln Lys Val Tyr Glu Gly Ala His Arg
```

```
                         180                 185                 190
Ala Val Glu Ile Glu Ala Leu Thr Pro His Ser Ser Tyr Cys Val Val
            195                 200                 205
Ala Glu Ile Tyr Gln Pro Met Leu Asp Arg Arg Ser Gln Arg Ser Glu
            210                 215                 220
Glu Arg Cys Val Glu Ile Pro
225                 230

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence:PCR Primer

<400> SEQUENCE: 36
cttgcaacca tgatgcctaa acattgc                                       27

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence:PCR Primer

<400> SEQUENCE: 37
atgatgccta aacattgctt tctagg                                        26

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence:PCR Primer

<400> SEQUENCE: 38
ggaactctgg ttgccagaca agcacac                                       27

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence:PCR Primer

<400> SEQUENCE: 39
caaggagaga tgtgtgcaga ttccatga                                      28
```

US 7,176,180 B2

TYPE 2 CYTOKINE RECEPTOR AND NUCLEIC ACIDS ENCODING SAME

RELATED APPLICATIONS

This application claims priority to U.S. Ser. No. 60/261,442, filed Jan. 12, 2001; U.S. Ser. No. 60/267,021, filed Feb. 6, 2001, and U.S. Ser. No. 60/270,835, filed Feb. 23, 2001. The contents of these applications are incorporated herein by reference in their entirety.

FIELD OF THE INVENTION

The invention relates generally to nucleic acids and polypeptides and more specifically to nucleic acids and polypeptides encoding type II cytokine receptors and extracellular counterparts of Type 2 cytokine receptors, as well as vectors, host cells, antibodies and recombinant methods for producing the polypeptides and polynucleotides.

BACKGROUND OF THE INVENTION

Cytokines are soluble proteins that influence the growth and differentiation of many cell types. Their receptors are composed of one or more integral membrane proteins that bind the cytokine with high affinity and transduce this binding event to the cell through the cytoplasmic portions of the certain receptor subunits. Cytokine receptors have been grouped into several classes on the basis of similarities in their extracellular ligand binding domains. For example, the receptor chains responsible for binding and/or transducing the effect of interferons (IFNs) are members of the type 2 cytokine receptor family (CRF2), based upon a characteristic 200–250 residue extracellular domain. The demonstrated in vivo activities of these interferons illustrate the clinical potential of, and need for, other cytokines, cytokine agonists, and cytokine antagonists.

Members of the CRF2 family have been reported to act as receptors for a variety of cytokines, including interferon alpha, interferon beta, interferon gamma, IL-10, IL-20, and IL-22. Recently identified members of the CRF2 family are candidate receptors for the IL-10-like molecules IL-19, AK155 and mda-7.

SUMMARY OF THE INVENTION

The invention is based, in part, upon the discovery of polynucleotide sequences encoding novel members of the CRF2 family.

Accordingly, in one aspect, the invention provides an isolated nucleic acid molecule that includes the sequence of SEQ ID NO:1, SEQ ID NO:3, SEQ ID NO:5, or SEQ ID NO:11, or a fragment, homolog, analog or derivative thereof. The nucleic acid can include, e.g., a nucleic acid sequence encoding a polypeptide at least 70%, e.g., 80%, 85%, 90%, 95%, 98%, or even 99% or more identical to a polypeptide that includes the amino acid sequences of SEQ ID NO:2, SEQ ID NO:4, SEQ ID NO:6, or SEQ ID NO:12. The nucleic acid can be, e.g., a genomic DNA fragment, or a cDNA molecule.

In some embodiments, the nucleic acid includes 5, 10, 15, 25, 50, 100, 150, 250, 500, 750, 1000, or 1500 nucleotides at the 5' side of the sequence including SEQ ID NO: 1, SEQ ID NO:3, SEQ ID NO:5, or SEQ ID NO:11. In some embodiments, the nucleic acid includes 5, 10, 15, 25, 50, 100, 150, 250, 500, 750, 1000, or 1500 nucleotides at the 3' side of the sequence including SEQ ID NO:1, SEQ ID NO:3, SEQ ID NO:5, or SEQ ID NO:11. In other embodiments, the nucleic acid includes 5, 10, 15, 25, 50, 100, 150, 250, 500, 750, 1000, or 1500 nucleotides at the 5' and 3' sides of the sequence including SEQ ID NO:1, SEQ ID NO:3, SEQ ID NO:5, or SEQ ID NO:11.

Also within the invention is a nucleic acid that encodes a polypeptide that includes amino acid sequences 21–66 of SEQ ID NO:2, e.g., a nucleic acids 62–197 of SEQ ID NO:1. Examples of such nucleic acid molecules are those that encode polypeptides with the amino acid sequences of SEQ ID NO:2, SEQ ID NO:4, or SEQ ID NO:6, e.g., nucleic acid sequences that include SEQ ID NOS. 1, 3, or 5.

In some embodiments, a CRF2-12 nucleic acid of the invention encodes a polypeptide that encodes a polypeptide that includes one or more of the following polypeptide sequences: MMPKHCL/FLG L/FLI, (SEQ ID NO:13), FQSRNFHNILH/QWQ A/PG (SEQ ID NO:14), SI/VY-FVQYKM/IYGQS/RQW (SEQ ID NO:15), TPRFTPW-WETKL/IDPPV (SEQ ID NO:16), LV/LYRVFT/IINNSLE-KEQKA/VYEG (SEQ ID NO:17), RAVEIEG/ALI/TPHSSYCVVAEM/IYQPM (SEQ ID NO:18), and DRRSP/QRSK/EERCVQ/EIP (SEQ ID NO:19).

In some embodiments, the nucleic acid includes 5, 10, 15, 25, 50, 100, 150, 250, 500, 750, 1000, or 1500 nucleotides at the 5' side of the sequence encoding a polypeptide that includes amino acid sequences 21–66 of SEQ ID NO:2. In some embodiments, the nucleic acid includes 5, 10, 15, 25, 50, 100, 150, 250, 500, 750, 1000, or 1500 nucleotides at the 3' side of the sequence encoding amino acids 21–66 of SEQ ID NO:2. In some embodiments, the nucleic acid includes 5, 10, 15, 25, 50, 100, 150, 250, 500, 750, 1000, or 1500 nucleotides at 5' side and the 3' sides of the sequence encoding amino acids 21–66 of SEQ ID NO:2.

Also included in the invention is a vector containing one or more of the nucleic acids described herein, and a cell containing the vectors or nucleic acids described herein.

The invention is also directed to host cells transformed with a vector comprising any of the nucleic acid molecules described above.

In another aspect, the invention includes a pharmaceutical composition that includes an CRF2-12 nucleic acid and a pharmaceutically acceptable carrier or diluent.

In a further aspect, the invention includes a substantially purified CRF2-12 polypeptide, e.g., any of the CRF2-12 polypeptides encoded by an CRF2-12 nucleic acid, and fragments, homologs, analogs, and derivatives thereof. The invention also includes a pharmaceutical composition that includes an CRF2-12 polypeptide and a pharmaceutically acceptable carrier or diluent.

In still a further aspect, the invention provides an antibody that binds specifically to an CRF2-12 polypeptide. The antibody can be, e.g., a monoclonal or polyclonal antibody, and fragments, homologs, analogs, and derivatives thereof. The invention also includes a pharmaceutical composition including CRF2-12 antibody and a pharmaceutically acceptable carrier or diluent. The invention is also directed to isolated antibodies that bind to an epitope on a polypeptide encoded by any of the nucleic acid molecules described above.

The invention also includes kits comprising any of the pharmaceutical compositions described above.

The invention further provides a method for producing an CRF2-12 polypeptide by providing a cell containing an CRF2-12 nucleic acid, e.g., a vector that includes an CRF2-12 nucleic acid, and culturing the cell under conditions sufficient to express the CRF2-12 polypeptide encoded by the nucleic acid. The expressed CRF2-12 polypeptide is then recovered from the cell. Preferably, the cell produces little or no endogenous CRF2-12 polypeptide. The cell can be, e.g., a prokaryotic cell or eukaryotic cell.

The invention is also directed to methods of identifying an CRF2-12 polypeptide or nucleic acid in a sample by contacting the sample with a compound that specifically binds to the polypeptide or nucleic acid, and detecting complex formation, if present.

The invention further provides methods of identifying a compound that modulates the activity of an CRF2-12 polypeptide by contacting an CRF2-12 polypeptide with a compound and determining whether the CRF2-12 polypeptide activity is modified.

The invention is also directed to compounds that modulate CRF2-12 polypeptide activity identified by contacting an CRF2-12 polypeptide with the compound and determining whether the compound modifies activity of the CRF2-12 polypeptide, binds to the CRF2-12 polypeptide, or binds to a nucleic acid molecule encoding an CRF2-12 polypeptide.

In another aspect, the invention provides a method of determining the presence of or predisposition of an CRF2-12-associated disorder in a subject. The method includes providing a sample from the subject and measuring the amount of CRF2-12 polypeptide in the subject sample. The amount of CRF2-12 polypeptide in the subject sample is then compared to the amount of CRF2-12 polypeptide in a control sample. An alteration in the amount of CRF2-12 polypeptide in the subject protein sample relative to the amount of CRF2-12 polypeptide in the control protein sample indicates the subject has a tissue proliferation-associated condition. A control sample is preferably taken from a matched individual, i.e., an individual of similar age, sex, or other general condition but who is not suspected of having a tissue proliferation-associated condition. Alternatively, the control sample may be taken from the subject at a time when the subject is not suspected of having a tissue proliferation-associated disorder. In some embodiments, the CRF2-12 is detected using an CRF2-12 antibody.

In a further aspect, the invention provides a method of determining the presence of or predisposition of an CRF2-12-associated disorder in a subject. The method includes providing a nucleic acid sample, e.g., RNA or DNA, or both, from the subject and measuring the amount of the CRF2-12 nucleic acid in the subject nucleic acid sample. The amount of CRF2-12 nucleic acid sample in the subject nucleic acid is then compared to the amount of an CRF2-12 nucleic acid in a control sample. An alteration in the amount of CRF2-12 nucleic acid in the sample relative to the amount of CRF2-12 in the control sample indicates the subject has a tissue proliferation-associated disorder.

In a still further aspect, the invention provides a method of treating or preventing or delaying a CRF2-12-associated disorder. The method includes administering to a subject in which such treatment or prevention or delay is desired an CRF2-12 nucleic acid, an CRF2-12 polypeptide, or an CRF2-12 antibody in an amount sufficient to treat, prevent, or delay a tissue proliferation-associated disorder in the subject. Examples of such disorders include rheumatoid arthritis and multiple sclerosis.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

The invention is based in part on the discovery of novel nucleic acid sequences encoding a polypeptide showing homology to CRF2 polypeptides. Included in the invention is a 696 nucleotide sequence encoding a soluble CRF2-like polypeptide (see Table 1; SEQ ID NO:1). The amino acid sequences of the encoded polypeptide is shown in Table 2 (SEQ ID NO:2). The predicted open reading frame encodes a 231 amino acid long secreted protein.

TABLE 1

ATGATGCCTAAACATTGCTTTCTAGGCTTCCTCATCAGTTTCTTCCTTACTGGTGTAGCA  (SEQ ID NO:1)

GGAACTCAGTCAACGCATGAGTCTCTGAAGCCTCAGAGGGTACAATTTCAGTCCCGAAAT

TTTCACAACATTTTGCAATGGCAGCCTGGGAGGGCACTTACTGGCAACAGCAGTGTCTAT

TTTGTGCAGTACAAAATATATGGACAGAGACAATGGAAAAATAAAGAAGACTGTTGGGGT

ACTCAAGAACTCTCTTGTGACCTTACCAGTGAAACCTCAGACATACAGGAACCTTATTAC

GGGAGGGTGAGGGCGGCCTCGGCTGGGAGCTACTCAGAATGGAGCATGACGCCGCGGTTC

ACTCCCTGGTGGGAAACAAAAATAGATCCTCCAGTCATGAATATAACCCAAGTCAATGGC

TCTTTGTTGGTAATTCTCCATGCTCCAAATTTACCATATAGATACCAAAAGGAAAAAAAT

GTATCTATAGAAGATTACTATGAACTACTATACCGAGTTTTTATAATTAACAATTCACTA

GAAAAGGAGCAAAAGGTTTATGAAGGGGCTCACAGAGCGGTTGAAATTGAAGCTCTAACA

CCACACTCCAGCTACTGTGTAGTGGCTGAAATATATCAGCCCATGTTAGACAGAAGAAGT

CAGAGAAGTGAAGAGAGATGTGTGGAAATTCCATGA

TABLE 2

MMPKHCFLGFLISFFLTGVAGTQSTHESLKPQRVQFQSRNFHNILQWQPGRALTGNSSVY  (SEQ ID NO:2)

FVQYKIYGQRQWKNKEDCWGTQELSCDLTSETSDIQEPYYGRVRAASAGSYSEWSMTPRF

TPWWETKIDPPVMNITQVNGSLLVILHAPNLPYRYQKEKNVSIEDYYELLYRVFIINNSL

EKEQKVYEGAHRAVEIEALTPHSSYCVVAEIYQPMLDRRSQRSEERCVEIP

Also included in the invention is a 792-nucleotide sequence encoding a soluble CRF2-like polypeptide (see Table 3; SEQ ID NO:3). While not wishing to be bound by theory, it is believed that the nucleotide sequence in Table 3 is the result of alternative splicing of the RNA transcribed from the CRF2-12 gene that also encodes the nucleotide sequence in Table 1. The amino acid sequences of the polypeptide encoded by the nucleotide sequence shown in Table 3 is shown in Table 4 (SEQ ID NO:4). The predicted open reading frame codes for a 263 amino acid long secreted protein. The nucleotide sequence of Table 3 has an extra exon of 96 nucleotides as compared to the nucleotide sequence shown in Table 1. The extra exon encodes a polypeptide that includes 32 amino acids not present in the polypeptide sequence shown in Table 2.

Also within the invention is a nucleic acid shown in Table 5. While not wishing to be bound by theory, it is believed that the nucleotide sequence in Table 5 is the result of alternative splicing of RNA transcribed from the CRF2-12 gene that also encodes the nucleotide sequences in Table 1 and 3. The disclosed nucleic acid encodes a polypeptide having the amino acid sequence shown in Table 6. As a result of alternative splicing that skips an exon and changes the frame of translation in the final exon, the amino acid sequence shown in Table 6 is shorter than the protein sequence in Table 2 and contains unique amino acids at its carboxy terminus.

TABLE 3

ATGATGCCTAAACATTGCTTTCTAGGCTTCCTCATCAGTTTCTTCCTTACTGGTGTAGC (SEQ ID NO:3)

AGGAACTCAGTCAACGCATGAGTCTCTGAAGCCTCAGAGGGTACAATTTCAGTCCCGAA

ATTTTCACAACATTTTGCAATGGCAGCCTGGGAGGGCACTTACTGGCAACAGCAGTGTC

TATTTTGTGCAGTACAAAATCATGTTCTCATGCAGCATGAAAAGCTCTCACCAGAAGCC

AAGTGGATGCTGGCAGCACATTTCTTGTAACTTCCCAGGCTGCAGAACATTGGCTAAAT

ATGGACAGAGACAATGGAAAAATAAAGAAGACTGTTGGGGTACTCAAGAACTCTCTTGT

GACCTTACCAGTGAAACCTCAGACATACAGGAACCTTATTACGGAGGGTGAGGGCGGC

CTCGGCTGGGAGCTACTCAGAATGGAGCATGACGCCGCGGTTCACTCCCTGGTGGGAAA

CAAAAATAGATCCTCCAGTCATGAATATAACCCAAGTCAATGGCTCTTTGTTGGTAATT

CTCCATGCTCCAAATTTACCATATAGATACCAAAAGGAAAAAAATGTATCTATAGAAGA

TTACTATGAACTACTATACCGAGTTTTTATAATTAACAATTCACTAGAAAAGGAGCAAA

AGGTTTATGAAGGGGCTCACAGAGCGGTTGAAATTGAAGCTCTAACACCACACTCCAGC

TACTGTGTAGTGGCTGAAATATATCAGCCCATGTTAGACAGAAGAAGTCAGAGAAGTGA

AGAGAGATGTGTGGAAATTCCATGA

TABLE 4

MMPKHCFLGFLISFFLTGVAGTQSTHESLKPQRVQFQSRNFHNILQWQPGRALTGNSSV (SEQ ID NO:4)

YFVQYKIMFSCSMKSSHQKPSGCWQHISCNFPGCRTLAKYGQRQWKNKEDCWGTQELSC

DLTSETSDIQEPYYGRVRAASAGSYSEWSMTPRFTPWWETKIDPPVMNITQVNGSLLVI

LHAPNLPYRYQKEKNVSIEDYYELLYRVFIINNSLEKEQKVYEGAHRAVEIEALTPHSS

YCVVAEIYQPMLDRRSQRSEERCVEIP

TABLE 5

(SEQ ID NO:5)
ATGATGCCTAAACATTGCTTTCTAGGCTTCCTCATCAGTTTCTTCCTTACTGGTGTAGCAGGAACTCAGTCA

ACGCATGAGTCTCTGAAGCCTCAGAGGGTACAATTTCAGTCCCGAAATTTTCACAACATTTTGCAATGGCAG

CCTGGGAGGGCACTTACTGGCAACAGCAGTGTCTATTTTGTGCAGTACAAAATATATGGACAGAGACAATGG

AAAAATAAAGAAGACTGTTGGGGTACTCAAGAACTCTCTTGTGACCTTACCAGTGAAACCTCAGACATACAG

GAACCTTATTACGGGAGGGTGAGGGCGGCCTCGGCTGGGAGCTACTCAGAATGGAGCATGACGCCGCGGTTC

ACTCCCTGGTGGGAAAGAGCAAAAGGTTTATGA

TABLE 6

(SEQ ID NO:6)
MMPKHCFLGFLISFFLTGVAGTQSTHESLKPQRVQFQSRNFHNILQWQPGRALTGNSSVYFVQYKIYGQRQW

KNKEDCWGTQELSCDLTSETSDIQEPYYGRVRAASAGSYSEWSMTPRFTPWWERAKGL

CRF2-like nucleic acids and polypeptides of the invention (including those shown in Tables 1–6) are referred to herein as "CRF2-12" nucleic acids and polypeptides.

The three disclosed CRF2-12 nucleic acids and encoded polypeptides share common sequences that correspond to two putative exons in a CRF2-12 gene. One includes an exon corresponding to exons 1–61 of SEQ ID NO:1. A second exon corresponds to nucleotides 62–197 of SEQ ID NO:1. These sequences are present in all the disclosed CRF2-12 nucleic acid sequences. Accordingly, a CRF2-12 nucleic acid can include one or both of these exons, and a CRF2-12 polypeptide can include the polypeptide sequence encoded by one or both of these exons. For example, included in the invention are CRF2-12 nucleic acids encoding polypeptides that include sequences homologous to amino acids 21–66 of SEQ ID NO:2, e.g., nucleic acids including nucleotides 62–197 of SEQ ID NO:1. Also within the invention are polypeptides that include sequences homologous to amino acids 21–66 of SEQ ID NO:2. Also included in the invention are CRF2-12 nucleic acids encoding polypeptides that include sequences homologous to amino acids 1–61 of SEQ ID NO:2, e.g., nucleic acids including nucleotides 1–61 of SEQ ID NO:1. Also within the invention are polypeptides that include sequences homologous to amino acids 1–61 of SEQ ID NO:2.

The sequences disclosed in Tables 1 and 2 were identified using a Hidden Markov model (HMM) constructed for the type II cytokine receptor family proteins. This HMM model was then used to search protein and nucleotide databases. The nucleic acid shown in Table 1 was assembled based on the compiled sequences.

A cDNA corresponding to the nucleic acid sequence shown Table 1 was identified using PCR amplification. PCR primers used included 5' CTTGCAACCATGATGC-CTAAACATTGC (SEQ ID NO:36) or ATGATGCCTAAA-CATTGCTTTCTAGG (SEQ ID NO:37) and 3' (TCATG-GAATTTCCACACATCTCTCTTCAC) (SEQ ID NO:7).

The primers were used to amplify cDNA species from a cDNA library. The RNA used to prepare the library was isolated from a mixed lymphocyte culture activated with PHA and PMA. A major species of ~700–750 bp was obtained after 40 cycles from five separate PCR reactions using the Clontech Advantage PCR kit. These five fragments were purified from preparative agarose gels using Sigma GenElute Minus EtBr Spin Columns. The fragments were subsequently ligated into Invitrogen vector pCR2.1 using the Invitrogen TA cloning kit. White transformants were obtained using Invitrogen TOPO 10 One Shot Chemical Transformation in conjunction with X-gal screening. Thirty white colonies were picked (six colonies from each transformation corresponding to an original 'PCR reaction') for culturing overnight in LB with ampicillin. Qiagen Spin Column Minipreps were done on 4.5 ml of cell culture and the subsequent DNA analyzed for inserts using EcoR1 restriction enzyme and agarose electrophoretic evaluation. Twenty three clones were evaluated for presence of an insert sequence. Three clones contained inserts having the nucleotide sequence shown in Table 1.

The polypeptide shown in Table 2 is the first member of the CRF2 family that does not contain a transmembrane domain. Thus, this polypeptide is likely secreted from a cell. The encoded ORF has the highest homology to ZcytoR7, ZcytoR11 and tissue factor. The polypeptide shown in Table 2 also shows high similarity to previously described class II cytokine receptors. The relatedness to previously described cytokine receptor factors is shown below.

| Matching Entry (in SwissProt + SpTrEMBL) | Begin–End | Description | Score | E Value |
|---|---|---|---|---|
| Q9YGC8 | [30–227] | INTERLEUKIN-10 RECEPTOR 2. | 73.4 | 1e-12 |
| I10R_MOUSE | [31–149] | INTERLEUKIN-10 RECEPTOR PRECURSOR (IL-10R). | 63.6 | 1e-09 |

-continued

| Matching Entry (in SwissProt + SpTrEMBL) | Begin–End | Description | Score | E Value |
|---|---|---|---|---|
| I10S_MOUSE | [6–227] | INTERLEUKIN-10 RECEPTOR BETA CHAIN PRECURSOR (IL-10R-B) (IL-10R2) (CYTOKINE RECEPTOR CLASS-II CRF2-4). | 62.8 | 2e-09 |
| I10S_MOUSE | [6–227] | INTERLEUKIN-10 RECEPTOR BETA CHAIN PRECURSOR (IL-10R-B) (IL-10R2) (CYTOKINE RECEPTOR CLASS-II CRF2-4). | 62.8 | 2e-09 |
| INR1_BOVIN | [22–209] [24–207] | INTERFERON-ALPHA/BETA RECEPTOR ALPHA CHAIN PRECURSOR (IFN-ALPHA-REC). | 62.5 | 2e-09 |
| TF_HUMAN | [11–228] | TISSUE FACTOR PRECURSOR (TF) (COAGULATION FACTOR III) (THROMBOPLASTIN) (CD142 ANTIGEN). | 61.7 | 4e-09 |
| CRF4_HUMAN | [31–227] | CYTOKINE RECEPTOR CLASS-II CRF2-4 PRECURSOR. | 61.7 | 4e-09 |
| Q9YHW0 | [31–229] [22–228] | INTERFERON ALPHA/BETA RECEPTOR 1. | 59.3 | 2e-08 |
| INR1_MOUSE | [27–228] | INTERFERON-ALPHA/BETA RECEPTOR ALPHA CHAIN PRECURSOR (IFN-ALPHA-REC). | 58.9 | 3e-08 |
| I10R_HUMAN | [1–230] | INTERLEUKIN-10 RECEPTOR PRECURSOR (IL-10R). | 57.0 | 1e-07 |
| TF_BOVIN | [11–167] | TISSUE FACTOR PRECURSOR (TF) (COAGULATION FACTOR III). | 55.0 | 4e-07 |
| INR1_SHEEP | [24-207] [22–209] | INTERFERON-ALPHA/BETA RECEPTOR ALPHA CHAIN PRECURSOR (IFN-ALPHA-REC) (INTERFERON ALPHA/BETA RECEPTOR-1). | 54.3 | 7e-07 |
| INR1_HUMAN | [31-207] [36–227] | INTERFERON-ALPHA/BETA RECEPTOR ALPHA CHAIN PRECURSOR (IFN-ALPHA-REC). | 54.3 | 7e-07 |
| INGR_HUMAN | [10–230] | INTERFERON-GAMMA RECEPTOR ALPHA CHAIN PRECURSOR (CDW119). | 51.2 | 6e-06 |
| Q9YHV9 | [31–228] | INTERFERON ALPHA/BETA RECEPTOR 2. | 49.2 | 2e-05 |
| TF_RABIT | [11–144] | TISSUE FACTOR PRECURSOR (TF) (COAGULATION FACTOR III). | 48.4 | 4e-05 |
| TF_RAT | [7–145] | TISSUE FACTOR PRECURSOR (TF) (COAGULATION FACTOR III). | 47.6 | 6e-05 |

The extent of the relatedness between the polypeptide shown in Table 2 and previously described type 2 cytokine receptor polypeptides ranges from 21%–34% identity. 40 to 47% of the amino acids are related as positive amino acids.

An alignment between the Q9YGC8 gallus gallus (chicken) interleukin-10 receptor 2 (5/1999) (SEQ ID NO:8) and amino acids 30–227 of the amino acid sequence (SEQ ID NO:33) shown in Table 2 is provided below. For the alignment shown, length=341, Score=73.4, bits (177.0), Expect=1e$^{-12}$, identities=56/200 (28%), and positives=92/200, (46%).

CTAAACATTGCTTTCTAGG (SEQ ID NO:9) and TCATGGAATTTCCACACATCTCTCTTCAC (SEQ ID NO:10). A cDNA containing the sequence presented in Table 3 was identified in pooled cDNA derived from a variety of human tissues. A cDNA containing the sequence presented in Table 5 was identified in a cDNA library derived from stomach tissue. The same ligation, transformation, screening and sequencing methods used for cloning DNA shown in Table 1 were used to produce a cDNA that includes the sequences that are presented in Tables 3 and 5.

```
Query:   30 KPQRVQFQSRNFHNILQWQPGRALTGNSSVYFVQYKIYGQRQWKNKEDCWGTQELSCDL   88
            KP+   +  S NF ++L W P   GN S Y VQ K I+ ++ + N       E CD+
Sbjct:   23 KPRNARISSVNFRSVLLWDPPGVRKGNLS-YTVQAKSIFPKQNFNNVTTNLNVTE--CDV  79

Query:   89 TSETSDIQEPYYGRVRAASAGSYSEWSMTPRFTPWWETKIDPPVMNITQVNGSLLVILHA  148
            +S   +    Y  RVR     +S+W++  RF P  +T I PP +N+    +G+L  V
Sbjct:   80 SS--LSVYGAYVLRVRTEWEDEHSDWAVV-RFKPMADTVIGPPSVNKSESGTLHVDFTG  136

Query:  149 PNLPYRYQKEKNVSIEDYY-ELLYRVFIINNSLEKEQKVYEGAHRAVEIEALTPHSSYCV  207
            P    + K    S++ YY  +YR+         K+    + H +  +  L P + YC+
Sbjct:  137 PAADREHDK---WSLKQYYGSWIYRILYWKKGSNKKVIHIDTKHNSEILSQLEPWTIYCI  193

Query:  208 VAEIYQPMLDRRSQRSEERC  227
             +   P  ++  +RS+E C
Sbjct:  194 QVQGVIPEWNKTGERSQELC  213
```

Additional CRF2-13 coding sequences were identified in PCR amplification assays using primers ATGATGC- A murine nucleotide sequence encoding a CRF2-12 polypeptide of the invention is shown in Table 7.

TABLE 7

(SEQ ID NO:11)
```
GGAACTCTGGTTGCCAGACAAGCACACTTGCAACCATGATGCCTAAGCATTGCCTTCTAGGTCTCCTCATCATACTCT
TGAGCAGTGCAACAGAAATACAACCAGCTCGTGTATCTCTGACGCCCCAGAAGGTCCGATTTCAGTCCAGAAATTTCC
ACAATATTTTGCACTGGCAAGCAGGGAGCTCTCTCCCCAGCAACAACAGCATCTACTTTGTGCAGTACAAGATGTATG
GACAGAGCCAATGGGAAGATAAAGTTGACTGCTGGGGGACCACGGCGCTCTTCTGTGACCTGACCAATGAAACCTTAG
ACCCATACGAGCTGTATTACGGGAGGGTGATGACGGCCTGTGCTGGACGCCACTCTGCCTGGACCAGGACACCCCGCT
TCACTCCATGGTGGGAAACAAAACTAGATCCTCCGGTCGTGACTATAACCCGAGTTAACGCATCTTTGCGGGTGCTTC
TCCGTCCTCCAGAGTTGCCAAATAGAAACCAAAGTGGAAAAAATGCATCCATGGAAACTTACTACGGCTTAGTATACA
GAGTTTTCACAATCAACAATTCACTAGAGAAGGAGCAAAAAGCCTATGAAGGGACTCAGAGAGCTGTTGAAATTGAAG
GTCTGATACCTCATTCCAGCTACTGCGTAGTGGCTGAAATGTACCAGCCCATGTTTGACAGAAGAAGCCCAAGAAGCA
AGGAGAGATGTGTGCAGATTCCATGA
```

The nucleotide sequence shown in Table 7 encodes a polypeptide of 230 amino acids having the amino acid sequence shown in Table 8.

TABLE 8

(SEQ ID NO:12)
```
MMPKHCLLGLLIILLSSATEIQPARVSLTPQKVRFQSRNFHNILHWQAGSSLPSNNSIYFVQYKMYGQSQWEDKVDCW
GTTALFCDLTNETLDPYELYYGRVMTACAGRHSAWTRTPRFTPWWETKLDPPVVTITRVNASLRVLLRPPELPNRNQS
GKNASMETYYGLVYRVFTINNSLEKEQKAYEGTQRAVEIEGLIPHSSYCVVAEMYQPMFDRRSPRSKERCVQIP
```

The murine sequence was identified using probes based on human CRF2-13 sequences. The isolation and characterization of the murine CRF2-13 sequence is disclosed in detail in the Examples, below.

A CRF2-12 nucleic acid, and the encoded polypeptide, according to the invention are useful in a variety of applications and contexts. For example, sequence comparison reveals that the disclosed CRF2-12 nucleic acids (Tables 1, 3, 5 and 7) encode secreted members of this family of receptors. One or more secreted receptor chains may be associated with, and/or modulate the activity of, another membrane bound member of CRF2, or a membrane bound receptor of another family. Alternatively, or in addition, the receptor chains disclosed herein may act alone or in combination with another soluble receptor. In effect, the receptor could also be a ligand.

It is also contemplated that the alternative forms polypeptides based on the polypeptide sequences shown in Tables 2, 4, and 6 may be expressed in different tissues and/or different conditions and thus carry out tissue specific affects.

A CRF2-12 polypeptide of the invention may additionally be used as a soluble receptor antagonist. Soluble receptor antagonists that block the activity of specific cytokines, e.g., TNF, are known in the art. A CRF2-12 polypeptide of the invention can similarly block the activity of a cytokine that acts through a CRF2 member. Examples of such polypeptides include IL-10, IL-19, IL-20, IL-22, AK155, mda-7 or an interferon, such as interferon alpha, interferon beta, or interferon gamma.

In one embodiment, a CRF2-12 polypeptide of the invention is used to antagonize the function of IL-22. IL-22 is distantly related in sequence to IL-10 and is produced by activated T cells. IL-22 signaling into a cell is mediated by its receptor chains, IL-22R and CRF2-4, both members of the CRF2 family. The CRF2-4 receptor was originally reported to serve as a second component in IL-10 signaling. IL-22 has been reported to inhibit IL-4 production from human Th2 T cells and to induce acute phase proteins in the liver of mice.

CRF2-12 nucleic acids and polypeptides according to the invention may additionally be used to identify cell types that make the invention or bind to the invention in a population of cells. The CRF2-12 nucleic acids and polypeptides can also be used for immunomodulation, inflammation, immunosuppression, allergy, asthma, autoimmunity (including rheumatoid arthritis and multiple sclerosis), repair of vascular smooth muscle cell after vascular injury or disease, transplantation and cancer based on the ligand that associates with this soluble receptor, alone or in conjunction with another receptor, and the impact that this ligand has on the above mechanisms and/or pathologies.

For example, a CRF2-12 polypeptide of the invention may exhibit one or more of the following activities: (1) modulation, e.g., it may antagonize a signal transduction pathway mediated by a cytokine (such as IL-10 or IL-22); (2) modulation of cytokine production and/or secretion (e.g., production and/or secretion of a proinflammatory cytokine); (3) modulation of lymphokine production and/or secretion; (4) modulation of expression or activity of nuclear transcription factors (5) competition with cytokine receptors for cytokine ligands; (6) modulation of cell proliferation, development or differentiation, e.g., cytokine-stimulated (such as IL-10 or IL-22) production, development, or differentiation; (7) modulation of cellular immune responses; modulation of cytokine-meditated proinflammatory actions; and/or promotion and/or potentiation of immune reactions.

A CRF2-12 polypeptide of the invention may directly, by association with a membrane bound receptor, or indirectly, by its association with a soluble ligand affect or effect one or more of the following cell types: circulating or tissue-associated cells: T cells, B cells, NK cells, NK T cells, dendritic cells, macrophages, monocytes, neutrophils, mast cells, basophils, eosinophils, as well as cells in the respiratory tract, pancreas, kidney, liver, small and large intestine. A CRF2-12 polypeptide of the invention may additionally modulate upregulation of humoral immune responses and cell-mediated immune reactions; modulate the synthesis of proinflammatory cytokines and chemokines; and modulate inflammatory responses associated with injury, sepsis, gastrointestinal and cardiovascular disease, or inflammation following surgery.

For efficient production of the protein, it is preferable to place the CRF2-12 sequences under the control of expression control sequences optimized for expression in a desired host. For example, the sequences may include optimized transcriptional and/or translational regulatory sequences (such as altered Kozak sequences). In addition, the mature amino terminus of a CRF2-12 protein may be operably linked to a non-CRF2-12 signal sequence based on a hypothetical or empirically determined of the mature amino terminal end of the protein.

A CRF2-12 fusion protein can be used to identify and determine binding partners using assays known in the art. These assays include, e.g., either histological, immunochemical, BIACORE or cell biology based assays.

Assays can also be performed in order to determine whether a CRF2-12 protein of the invention associates with cell types that already express other members of the CRF2 family. A CRF2-12 of the invention can also be examined for its ability to modulate the activity of known or novel cytokines (e.g., by inhibiting or otherwise antagonizing the functions of a cytokine).

For example, several novel IL-10 like molecules have been cloned. IL-22 is one of these molecules. It has been reported that this molecule blocks the production of IL-4 by Th2 cells (human) and initiates an acute phase response (mice). A finding that CRF2-12 binds to and inhibits IL-22 (or other IL-10 like molecules) indicates a CRF2-12 invention can be used to treat or prevent diseases associated with high levels of the IL-22 polypeptide.

It is also anticipated that a CRF2-12 polypeptide of the invention associates with other receptors and/or their associated cytokines within the CRF2 family. For example, a CRF2-12 of the invention may associate with either chain of the IL-22R and affect the function of the receptor or the IL-22 ligand.

CRF2-12 Nucleic Acids

The nucleic acids of the invention include those that encode a CRF2-12 polypeptide or protein. As used herein, the terms polypeptide and protein are interchangeable.

In some embodiments, a CRF2-12 nucleic acid encodes a mature CRF2-12 polypeptide. As used herein, a "mature" form of a polypeptide or protein described herein relates to the product of a naturally occurring polypeptide or precursor form or proprotein. The naturally occurring polypeptide, precursor or proprotein includes, by way of nonlimiting example, the full length gene product, encoded by the corresponding gene. Alternatively, it may be defined as the polypeptide, precursor or proprotein encoded by an open reading frame described herein. The product "mature" form arises, again by way of nonlimiting example, as a result of one or more naturally occurring processing steps that may take place within the cell in which the gene product arises. Examples of such processing steps leading to a "mature" form of a polypeptide or protein include the cleavage of the N-terminal methionine residue encoded by the initiation codon of an open reading frame, or the proteolytic cleavage of a signal peptide or leader sequence. Thus a mature form arising from a precursor polypeptide or protein that has residues 1 to N, where residue 1 is the N-terminal methionine would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

Among the CRF2-12 nucleic acids is the nucleic acid whose sequence is provided in SEQ ID NO:1, SEQ ID NO:3, SEQ ID NO:5, SEQ ID NO:11 or a fragment thereof. Additionally, the invention includes mutant or variant nucleic acids of SEQ ID NO:1, SEQ ID NO:3, SEQ ID NO:5, or SEQ ID NO:11, or a fragment thereof, any of whose bases may be changed from the corresponding bases, while still encoding a protein that maintains at least one of its CRF2-12-like activities and physiological functions (e.g., binding cytokines). The invention further includes the complement of the nucleic acid sequence of the disclosed CRF2-12 nucleic acids, including fragments, derivatives, analogs and homologs thereof. The invention additionally includes nucleic acids or nucleic acid fragments, or complements thereto, whose structures include chemical modifications.

The invention also includes nucleic acids that encode a CRF2-12 polypeptide having one or more of the polypeptide sequences MMPKHCL/FLG L/FLI, (SEQ ID NO:13), FQS-RNFHNILH/QWQ A/PG (SEQ ID NO:14), SI/VY-FVQYKM/IYGQS/RQW (SEQ ID NO:15), TPRFTPW-WETKL/IDPPV (SEQ ID NO:16), LV/LYRVFT/IINNSLEKEQKA/VYEG (SEQ ID NO:17), RAVEIEG/ALI/TPHSSYCVVAEM/IYQPM (SEQ ID NO:18), and DRRSP/QRSK/EERCVQ/EIP (SEQ ID NO:19).

One aspect of the invention pertains to isolated nucleic acid molecules that encode CRF2-12 proteins or biologically active portions thereof. Also included are nucleic acid fragments sufficient for use as hybridization probes to identify CRF2-12-encoding nucleic acids (e.g., CRF2-12 mRNA) and fragments for use as polymerase chain reaction (PCR) primers for the amplification or mutation of CRF2-12 nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

"Probes" refer to nucleic acid sequences of variable length, preferably between at least about 10 nucleotides (nt), 100 nt, or as many as about, e.g., 6,000 nt, depending on use. Probes are used in the detection of identical, similar, or complementary nucleic acid sequences. Longer length probes are usually obtained from a natural or recombinant source, are highly specific and much slower to hybridize than oligomers. Probes may be single- or double-stranded and designed to have specificity in PCR, membrane-based hybridization technologies, or ELISA-like technologies.

An "isolated" nucleic acid molecule is one that is separated from other nucleic acid molecules that are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i e., sequences located at the 5' and 3' ends of the nucleic acid) in the genomic DNA of the organism from which the nucleic acid is derived. For example, in various embodiments, the isolated CRF2-12 nucleic acid molecule can contain less than about 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the present invention, e.g., a nucleic acid molecule having the nucleotide sequence of SEQ ID NO:1, SEQ ID NO:3, SEQ ID NO:5, or SEQ ID NO:11, or a complement thereof, can be isolated using standard molecular biology techniques and the sequence information provided herein. Using all or a portion of the nucleic acid sequence of SEQ ID NO:1, SEQ ID NO:3, SEQ ID NO:5, or SEQ ID NO:11 as a hybridization probe, CRF2-12 nucleic acid sequences can be isolated using standard hybridization and cloning techniques (e.g., as described in Sambrook et al., eds., MOLECULAR CLONING: A LABORATORY MANUAL $2^{nd}$ Ed., Cold Spring Harbor Laboratory Press, Cold Spring Harbor. N.Y., 1989; and Ausubel, et al. eds., CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to CRF2-12 nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment, an oligonucleotide comprising a nucleic acid molecule less than 100 nt in length would further comprise at lease 6 contiguous nucleotides of SEQ ID NO:1, SEQ ID NO:3, SEQ ID NO:5, SEQ ID NO:11, or a complement thereof. Oligonucleotides may be chemically synthesized and may be used as probes.

In another embodiment, an isolated nucleic acid molecule of the invention comprises a nucleic acid molecule that is a complement of the nucleotide sequence shown in SEQ ID NO:1, SEQ ID NO:3, SEQ ID NO:5, SEQ ID NO:11, or a portion of this nucleotide sequence. A nucleic acid molecule that is complementary to the nucleotide sequence shown in SEQ ID NO:1, SEQ ID NO:3, SEQ ID NO:5, or SEQ ID NO:11 is one that is sufficiently complementary to the nucleotide sequence shown in SEQ ID NO:1, SEQ ID NO:3, SEQ ID NO:5, or SEQ ID NO:11 that it can hydrogen bond with little or no mismatches to the nucleotide sequence shown in SEQ ID NO:1, SEQ ID NO:3, SEQ ID NO:5, or SEQ ID NO:11, thereby forming a stable duplex.

As used herein, the term "complementary" refers to Watson-Crick or Hoogsteen base pairing between nucleotide units of a nucleic acid molecule, and the term "binding" means the physical or chemical interaction between two polypeptides or compounds or associated polypeptides or compounds or combinations thereof. Binding includes ionic, non-ionic, Von der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the nucleic acid sequence of SEQ ID NO:1, SEQ ID NO:3, SEQ ID NO:5, or SEQ ID NO:11, or SEQ ID NO:11, e.g., a fragment that can be used as a probe or primer, or a fragment encoding a biologically active portion of CRF2-12. Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, 85%, 90%, 95%, 98%, or even 99% identity (with a preferred identity of 80–99%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (Adv. Appl. Math., 1981, 2: 482–489, which is incorporated herein by reference in its entirety).

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of a CRF2-12 polypeptide. Isoforms can be expressed in different tissues of the same organism as a result of, for example, alternative splicing of RNA. Alternatively, isoforms can be encoded by different genes. In the present invention, homologous nucleotide sequences include nucleotide sequences encoding for a CRF2-12 polypeptide of species other than humans, including, but not limited to, mammals, and thus can include, e.g., mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the nucleotide sequence encoding human CRF2-12 protein. Homologous nucleic acid sequences include those nucleic acid sequences that encode conservative amino acid substitutions (see below) in SEQ ID NO:2, SEQ ID NO:4, SEQ ID NO:6, or SEQ ID NO:12, as well as a polypeptide having CRF2-12 activity. For example, a CRF2-12 nucleic acid of the invention includes a nucleic acid that encodes a polypeptide having one or more, e.g., two, three, five, ten, 15, 20, or 25 or more substitutions in its amino acid sequence relative to amino acids 21–62 of SEQ ID NO:2.

Biological activities of the CRF2-12 proteins are described below. A homologous amino acid sequence does not encode the amino acid sequence of a human CRF2-12 polypeptide.

The nucleotide sequence determined from the cloning of the human CRF2-12 gene allows for the generation of probes and primers designed for use in identifying and/or cloning CRF2-12 homologues in other cell types, e.g., from other tissues, as well as CRF2-12 homologues from other mammals. The probe/primer typically comprises a substantially purified oligonucleotide. The oligonucleotide typically comprises a region of nucleotide sequence that hybridizes under stringent conditions to at least about 12, 25, 50, 100, 150, 200, 250, 300, 350 or 400 or more consecutive sense strand nucleotide sequence of SEQ ID NO:1, SEQ ID NO:3, SEQ ID NO:5, or SEQ ID NO:11; or an anti-sense strand nucleotide sequence of one of these sequences; or of a naturally occurring mutant of one of these.

Probes based on the human CRF2-12 nucleotide sequence can be used to detect transcripts or genomic sequences encoding the same or homologous proteins. In various embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a CRF2-12 protein, such as by measuring a level of a CRF2-12-encoding nucleic acid in a sample of cells from a subject e.g., detecting CRF2-12 mRNA levels or determining whether a genomic CRF2-12 gene has been mutated or deleted.

A "polypeptide having a biologically active portion of CRF2-12" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of CRF2-12" can be prepared by isolating a portion of SEQ ID NO:1, SEQ ID NO:3, SEQ ID NO:5, or SEQ ID NO:11, that encodes a polypeptide having a CRF2-12 biological activity (biological activities of the CRF2-12 proteins are described below), expressing the encoded portion of CRF2-12 protein (e.g., by recombinant expression in vitro) and assessing the activity of the encoded portion of CRF2-12. For example, a nucleic acid fragment encoding a biologically active portion of CRF2-12 can optionally include an ATP-binding domain. In another embodiment, a nucleic acid fragment encoding a biologically active portion of CRF2-12 includes one or more regions.

CRF2-12 Variants

The invention further encompasses nucleic acid molecules that differ from the nucleotide sequences shown in SEQ ID NO:1, SEQ ID NO:3, SEQ ID NO:5, or SEQ ID NO:11 due to the degeneracy of the genetic code. These nucleic acids thus encode the same CRF2-12 protein as that encoded by the nucleotide sequence shown in SEQ ID NO:1, SEQ ID NO:3, SEQ ID NO:5, or SEQ ID NO:11, e.g. the polypeptide of SEQ ID NO:2, SEQ ID NO:4, SEQ ID NO:6, or SEQ ID NO:12, respectively. In another embodiment, an isolated nucleic acid molecule of the invention has a nucleotide sequence encoding a protein having an amino acid sequence shown in SEQ ID NO:2, SEQ ID NO:4, SEQ ID NO:6, or SEQ ID NO:12, respectively.

In addition to the human CRF2-12 nucleotide sequence shown in SEQ ID NO:1, SEQ ID NO:3, SEQ ID NO:5, SEQ ID NO:7, or SEQ ID NO:11, it will be appreciated by those skilled in the art that DNA sequence polymorphisms that lead to changes in the amino acid sequences of CRF2-12 may exist within a population (e.g., the human population). Such genetic polymorphism in the CRF2-12 gene may exist among individuals within a population due to natural allelic variation. As used herein, the terms "gene" and "recombinant gene" refer to nucleic acid molecules comprising an open reading frame encoding a CRF2-12 protein, preferably a mammalian CRF2-12 protein. Such natural allelic variations can typically result in 1–5% variance in the nucleotide sequence of the CRF2-12 gene. Any and all such nucleotide variations and resulting amino acid polymorphisms in CRF2-12 that are the result of natural allelic variation and that do not alter the functional activity of CRF2-12 are intended to be within the scope of the invention.

Moreover, nucleic acid molecules encoding CRF2-12 proteins from other species, and thus that have a nucleotide sequence that differs from the human sequence of SEQ ID NO:1, SEQ ID NO:3, or SEQ ID NO:5, or the murine sequence of SEQ ID NO:11, are intended to be within the scope of the invention. Nucleic acid molecules corresponding to natural allelic variants and homologues of the CRF2-12 cDNAs of the invention can be isolated based on their homology to the human CRF2-12 nucleic acids disclosed herein using the human cDNAs, or a portion thereof, as a hybridization probe according to standard hybridization techniques under stringent hybridization conditions. For example, a soluble human or murine CRF2-12 cDNA can be isolated based on its homology to human membrane-bound CRF2-12. Likewise, a membrane-bound human or murine CRF2-12 cDNA can be isolated based on its homology to soluble human CRF2-12.

Accordingly, in another embodiment, an isolated nucleic acid molecule of the invention is at least 6 nucleotides in length and hybridizes under stringent conditions to the nucleic acid molecule comprising the nucleotide sequence of SEQ ID NO:1, SEQ ID NO:3, SEQ ID NO:5, or SEQ ID NO:11. In another embodiment, the nucleic acid is at least 10, 25, 50, 100, 250, 500 or 750 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding CRF2-12 proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point ($T_m$) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in CURRENT PROTOCOLS IN MOLECULAR BIOLOGY, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. An isolated nucleic acid molecule of the invention that hybridizes under stringent conditions to the sequence of SEQ ID NO:1, SEQ ID NO:3, SEQ ID NO:5, or SEQ ID NO:11, corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NO:1, SEQ ID NO:3, SEQ ID NO:5, or SEQ ID NO:11, or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well known in the art. See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY.

In a third embodiment, a nucleic acid that is hybridizable to the nucleic acid molecule comprising the nucleotide sequence of SEQ ID NO:1, SEQ ID NO:3, SEQ ID NO:5, or SEQ ID NO:11, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981, *Proc Natl Acad Sci USA* 78: 6789–6792.

Conservative Mutations

In addition to naturally-occurring allelic variants of the CRF2-12 sequence that may exist in the population, the skilled artisan will further appreciate that changes can be introduced by mutation into the nucleotide sequence of SEQ ID NO:1, SEQ ID NO:3, SEQ ID NO:5, or SEQ ID NO:11, thereby leading to changes in the amino acid sequence of the encoded CRF2-12 protein, without altering the functional ability of the CRF2-12 protein. For example, nucleotide substitutions leading to amino acid substitutions at "non-essential" amino acid residues can be made in the sequence of SEQ ID NO:1, SEQ ID NO:3, SEQ ID NO:5, or SEQ ID NO:11. A "non-essential" amino acid residue is a residue that can be altered from the wild-type sequence of CRF2-12 without altering the biological activity, whereas an "essential" amino acid residue is required for biological activity. For example, amino acid residues that are conserved among the CRF2-12 proteins of the present invention, are predicted to be particularly unamenable to alteration.

Another aspect of the invention pertains to nucleic acid molecules encoding CRF2-12 proteins that contain changes in amino acid residues that are not essential for activity. Such CRF2-12 proteins differ in amino acid sequence from SEQ ID NO:2, SEQ ID NO:4, or SEQ ID NO:12, yet retain biological activity. In one embodiment, the isolated nucleic acid molecule comprises a nucleotide sequence encoding a protein, wherein the protein comprises an amino acid sequence at least about 75% homologous to one of these amino acid sequences. Preferably, the protein encoded by the nucleic acid is at least about 80% homologous to one of these amino acid sequences, more preferably at least about 90%, 95%, 98%, and most preferably at least about 99% homologous to one of these amino acid sequences.

An isolated nucleic acid molecule encoding a CRF2-12 protein homologous to the protein of SEQ ID NO:2, SEQ ID NO:4, SEQ ID NO:6, or SEQ ID NO:12 can be created by introducing one or more nucleotide substitutions, additions or deletions into the nucleotide sequence of SEQ ID NO:1, SEQ ID NO:3, SEQ ID NO:5, or SEQ ID NO:11, such that one or more amino acid substitutions, additions or deletions are introduced into the encoded protein.

Mutations can be introduced into the a CRF2-12 nucleotide sequence (e.g., SEQ ID NO:1, SEQ ID NO:3, SEQ ID NO:5, or SEQ ID NO:11) by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in CRF2-12 is replaced with another amino acid residue from the same side chain family. Alternatively, in another embodiment, mutations can be introduced randomly along all or part of a CRF2-12 coding sequence, such as by saturation mutagenesis, and the resultant mutants can be screened for CRF2-12 biological activity to identify mutants that retain activity. Following mutagenesis of SEQ ID NO:1, SEQ ID NO:3, SEQ ID NO:5, or SEQ ID NO:11 the encoded protein can be expressed by any recombinant technology known in the art and the activity of the protein can be determined.

In one embodiment, a mutant CRF2-12 protein can be assayed for (1) the ability to form protein:protein interactions with other CRF2-12 proteins, other cell-surface proteins, or biologically active portions thereof, (2) complex formation between a mutant CRF2-12 protein and a CRF2-12 receptor; (3) the ability of a mutant CRF2-12 protein to bind to an intracellular target protein or biologically active portion thereof; (e.g., avidin proteins); (4) the ability to bind CRF2-12 protein; (5) the ability to specifically bind an anti-CRE2-12 protein antibody, or (6) the ability to bind to a cytokine polypeptide such as IL-22.

Antisense CRF2-12 Nucleic Acids

Another aspect of the invention pertains to isolated antisense nucleic acid molecules that are hybridizable to or complementary to the nucleic acid molecule comprising the nucleotide sequence of SEQ ID NO:1, SEQ ID NO:3, SEQ ID NO:5, or SEQ ID NO:11, or fragments, analogs or derivatives thereof. An "antisense" nucleic acid comprises a nucleotide sequence that is complementary to a "sense" nucleic acid encoding a protein. e. g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire CRF2-12 coding strand, or to only a portion thereof. Nucleic acid molecules encoding fragments, homologs, derivatives and analogs of a CRF2-12 protein of SEQ ID NO:2, SEQ ID NO:4, or SEQ ID NO:6, or antisense nucleic acids complementary to a CRF2-12 nucleic acid sequence of SEQ ID NO:1, SEQ ID NO:3, SEQ ID NO:5, or SEQ ID NO:11 are additionally provided.

In one embodiment, an antisense nucleic acid molecule is antisense to a "coding region" of the coding strand of a nucleotide sequence encoding CRF2-12. The term "coding region" refers to the region of the nucleotide sequence comprising codons which are translated into amino acid residues (e.g., the protein coding region of human CRF2-12 corresponds to SEQ ID NO:2, SEQ ID NO:4, SEQ ID NO:6, or SEQ ID NO:12). In another embodiment, the antisense nucleic acid molecule is antisense to a "noncoding region" of the coding strand of a nucleotide sequence encoding CRF2-12. The term "noncoding region" refers to 5' and 3' sequences which flank the coding region that are not translated into amino acids (i.e., also referred to as 5' and 3' untranslated regions).

Given the coding strand sequences encoding CRF2-12 disclosed herein (e.g., SEQ ID NO:1, SEQ ID NO:3, SEQ ID NO:5, or SEQ ID NO:11), antisense nucleic acids of the invention can be designed according to the rules of Watson and Crick or Hoogsteen base pairing. The antisense nucleic acid molecule can be complementary to the entire coding region of CRF2-12 mRNA, but more preferably is an oligonucleotide that is antisense to only a portion of the coding or noncoding region of CRF2-12 mRNA. For example, the antisense oligonucleotide can be complementary to the region surrounding the translation start site of CRF2-12 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a CRF2-12 protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res* 15: 6625–6641). The antisense nucleic acid molecule can also comprise a 2'-o-methylribonucleotide (Inoue et al. (1987) *Nucleic Acids Res* 15: 6131–6148) or a chimeric RNA-DNA analogue (Inoue et al. (1987) *FEBS Lett* 215: 327–330).

Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

CRF2-12 Ribozymes and PNA Moieties

In still another embodiment, an antisense nucleic acid of the invention is a ribozyme. Ribozymes are catalytic RNA molecules with ribonuclease activity that are capable of cleaving a single-stranded nucleic acid, such as a mRNA, to which they have a complementary region. Thus, ribozymes (e.g., hammerhead ribozymes (described in Haselhoff and Gerlach (1988) *Nature* 334:585–591)) can be used to catalytically cleave CRF2-12 mRNA transcripts to thereby inhibit translation of CRF2-12 mRNA. A ribozyme having specificity for a CRF2-12-encoding nucleic acid can be designed based upon the nucleotide sequence of a CRF2-12 DNA disclosed herein (i.e., SEQ ID NO:1, SEQ ID NO:3, SEQ ID NO:5, or SEQ ID NO:11). For example, a derivative of a Tetrahymena L-19 IVS RNA can be constructed in which the nucleotide sequence of the active site is complementary to the nucleotide sequence to be cleaved in a CRF2-12-encoding mRNA. See, e.g., Cech et al. U.S. Pat. No. 4,987,071; and Cech et al. U.S. Pat. No. 5,116,742. Alternatively, CRF2-12 mRNA can be used to select a catalytic RNA having a specific ribonuclease activity from a pool of RNA molecules. See, e.g., Bartel et al., (1993) *Science* 261:1411–1418.

Alternatively, CRF2-12 gene expression can be inhibited by targeting nucleotide sequences complementary to the regulatory region of the CRF2-12 (e.g., the CRF2-12 promoter and/or enhancers) to form triple helical structures that prevent transcription of the CRF2-12 gene in target cells. See generally, Helene. (1991) *Anticancer Drug Des.* 6: 569–84; Helene. et al. (1992) *Ann. N.Y. Acad. Sci.* 660: 27–36; and Maher (1992) *Bioassays* 14: 807–15.

In various embodiments, the nucleic acids of CRF2-12 can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorg Med Chem* 4: 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) *PNAS* 93: 14670–675.

PNAs of CRF2-12 can be used in therapeutic and diagnostic applications. For example, PNAs can be used as antisense or antigene agents for sequence-specific modulation of gene expression by, e.g., inducing transcription or translation arrest or inhibiting replication. PNAs of CRF2-12 can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) above); or as probes or primers for DNA sequence and hybridization (Hyrup et al. (1996), above; Perry-O'Keefe (1996), above).

In another embodiment, PNAs of CRF2-12 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of CRF2-12 can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) *Nucl Acids Res* 24: 3357–63. For example, a DNA chain can be synthesized on a solid support using standard phosphoramidite coupling chemistry, and modified nucleoside analogs, e.g., 5'-(4-methoxytrityl) amino-5'-deoxy-thymidine phosphoramidite, can be used between the PNA and the 5' end of DNA (Mag et al. (1989) *Nucl Acid Res* 17: 5973–88). PNA monomers are then coupled in a stepwise manner to produce a chimeric molecule with a 5' PNA segment and a 3' DNA segment (Finn et al. (1996) above). Alternatively, chimeric molecules can be synthesized with a 5' DNA segment and a 3' PNA segment. See, Petersen et al. (1975) *Bioorg Med Chem Lett* 5: 1119–11124.

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. U.S.A.* 86:6553–6556; Lemaitre et al., 1987, *Proc. Natl. Acad. Sci.* 84:648–652; PCT Publication No. WO88/09810) or the blood-brain barrier (see, e.g., PCT Publication No. WO89/10134). In addition, oligonucleotides can be modified with hybridization triggered cleavage agents (See, e.g., Krol et al., 1988, *BioTechniques* 6:958–976) or intercalating agents. (See, e.g., Zon, 1988, *Pharm. Res.* 5: 539–549). To this end, the oligonucleotide may be conjugated to another molecule, e.g., a peptide, a hybridization triggered cross-linking agent, a transport agent, a hybridization-triggered cleavage agent, etc.

CRF2-12 Polypeptides

A CRF2-12 polypeptide of the invention includes the CRF2-12-like protein whose sequence is provided in SEQ ID NO:2, SEQ ID NO:4, SEQ ID NO:6, or SEQ ID NO:12. The Hi invention also CRF2-12 polypeptide encoded by the CRF2-12 nucleic acids disclosed herein. For example, a CRF2-12 polypeptide includes a mutant or variant protein any of whose residues may be changed from the corresponding residue shown in these polypeptide sequences while still encoding a protein that maintains its CRF2-12-like activities and physiological functions, or a functional fragment thereof. In some embodiments, up to 20% or more of the residues may be so changed in the mutant or variant protein. In some embodiments, the CRF2-12 polypeptide according to the invention is a mature polypeptide.

In general, a CRF2-12-like variant that preserves CRF2-12-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated CRF2-12 proteins, and biologically active portions thereof, or derivatives, fragments, analogs or homologs thereof. Also provided are polypeptide fragments suitable for use as immunogens to raise anti-CRF2-12 antibodies. In one embodiment, native CRF2-12 proteins can be isolated from cells or tissue sources by an appropriate purification scheme using standard protein purification techniques. In another embodiment, CRF2-12 proteins are produced by recombinant DNA techniques. Alternative to recombinant expression, a CRF2-12 protein or polypeptide can be synthesized chemically using standard peptide synthesis techniques.

An "isolated" or "purified" protein or biologically active portion thereof is substantially free of cellular material or other contaminating proteins from the cell or tissue source from which the CRF2-12 protein is derived, or substantially free from chemical precursors or other chemicals when chemically synthesized. The language "substantially free of cellular material" includes preparations of CRF2-12 protein in which the protein is separated from cellular components of the cells from which it is isolated or recombinantly produced. In one embodiment, the language "substantially free of cellular material" includes preparations of CRF2-12 protein having less than about 30% (by dry weight) of non-CRF2-12 protein (also referred to herein as a "contaminating protein"), more preferably less than about 20% of non-CRF2-12 protein, still more preferably less than about 10% of non-CRF2-12 protein, and most preferably less than about 5% non-CRF2-12 protein. When the CRF2-12 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of CRF2-12 protein in which the protein is separated from chemical precursors or other chemicals that are involved in the synthesis of the protein. In one embodiment, the language "substantially free of chemical precursors or other chemicals" includes preparations of CRF2-12 protein having less than about 30% (by dry weight) of chemical precursors or non-CRF2-12 chemicals, more preferably less than about 20% chemical precursors or non-CRF2-12 chemicals, still more preferably less than about 10% chemical precursors or non-CRF2-12 chemicals, and most preferably less than about 5% chemical precursors or non-CRF2-12 chemicals.

Biologically active portions of a CRF2-12 protein include peptides comprising amino acid sequences sufficiently homologous to or derived from the amino acid sequence of the CRF2-12 protein, e.g. the amino acid sequence shown in SEQ ID NO:2, SEQ ID NO:4, SEQ ID NO:6, or SEQ ID NO:12, that include fewer amino acids than the full length CRF2-12 proteins, and exhibit at least one activity of a CRF2-12 protein (e.g., binding a cytokine such as IL-10 or IL-22). Typically, biologically active portions comprise a domain or motif with at least one activity of the CRF2-12 protein. A biologically active portion of a CRF2-12 protein can be a polypeptide which is, for example, 10, 25, 50, 100 or more amino acids in length.

A biologically active portion of a CRF2-12 protein of the present invention may contain at least one of the above-identified domains conserved between the CRF2-12 proteins. Moreover, other biologically active portions, in which other regions of the protein are deleted, can be prepared by recombinant techniques and evaluated for one or more of the functional activities of a native CRF2-12 protein.

In an embodiment, the CRF2-12 protein has an amino acid sequence shown in SEQ ID NO:2, SEQ ID NO:4, SEQ ID NO:6, or SEQ ID NO:12. In other embodiments, the CRF2-12 protein is substantially homologous to SEQ ID NO:2, SEQ ID NO:4, SEQ ID NO:6, or SEQ ID NO:12 and retains the functional activity of the protein of SEQ ID NO:2, SEQ ID NO:4, SEQ ID NO:6, or SEQ ID NO:12, yet differs in amino acid sequence due to natural allelic variation or mutagenesis, as described in detail below. Accordingly, in another embodiment, the CRF2-12 protein is a protein that comprises an amino acid sequence at least about 45% homologous to the amino acid sequence of SEQ ID NO:2, SEQ ID NO:4, SEQ ID NO:6 or SEQ ID NO:12 and retains the functional activity of the CRF2-12 proteins of SEQ ID NO:2, SEQ ID NO:4, SEQ ID NO:6 or SEQ ID NO:12.

A CRF2-12 polypeptide of the invention also includes a polypeptide having one or more. e.g., two, three, five, ten, 15, 20, or 25 or more substitutions in its amino acid sequence relative to amino acids 21–62 of SEQ ID NO:2.

Determining Homology between Two or More Sequence

To determine the percent homology of two amino acid sequences or of two nucleic acids, the sequences are aligned for optimal comparison purposes (e.g., gaps can be introduced in either of the sequences being compared for optimal alignment between the sequences). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch 1970 *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NO:1, SEQ ID NO:3, SEQ ID NO:5, or SEQ ID NO:11.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region. The term "percentage of positive residues" is calculated by comparing two optimally aligned sequences over that region of comparison, determining the number of positions at which the identical and conservative amino acid substitutions, as defined above, occur in both sequences to yield the number of matched positions, dividing the number of matched positions by the total number of positions in the region of comparison (i.e., the window size), and multiplying the result by 100 to yield the percentage of positive residues.

Chimeric and Fusion Proteins

The invention also provides CRF2-12 chimeric or fusion proteins. As used herein, a CRF2-12 "chimeric protein" or "fusion protein" comprises a CRF2-12 polypeptide operatively linked to a non-CRF2-12 polypeptide. An "CRF2-12 polypeptide" refers to a polypeptide having an amino acid sequence corresponding to CRF2-12, whereas a "non-CRF2-12 polypeptide" refers to a polypeptide having an amino acid sequence corresponding to a protein that is not substantially homologous to the CRF2-12 protein, e.g., a protein that is different from the CRF2-12 protein and that is derived from the same or a different organism. Within a CRF2-12 fusion protein the CRF2-12 polypeptide can correspond to all or a portion of a CRF2-12 protein. In one embodiment, a CRF2-12 fusion protein comprises at least one biologically active portion of a CRF2-12 protein. In another embodiment, a CRF2-12 fusion protein comprises at least two biologically active portions of a CRF2-12 protein. Within the fusion protein, the term "operatively linked" is intended to indicate that the CRF2-12 polypeptide and the non-CRF2-12 polypeptide are fused in-frame to each other. The non-CRF2-12 polypeptide can be fused to the N-terminus or C-terminus of the CRF2-12 polypeptide.

For example, in one embodiment a CRF2-12 fusion protein comprises a CRF2-12 polypeptide operably linked to either an extracellular domain of a second protein, i.e., non-CRF2-12 protein, or to the transmembrane and intracellular domain of a second protein, i.e., non-CRF2-12 protein. Such fusion proteins can be further utilized in screening assays for compounds that modulate CRF2-12 activity (such assays are described in detail below).

In another embodiment, the fusion protein is a GST-CRF2-12 fusion protein in which the CRF2-12 sequences are fused to the C-terminus of the GST (i.e., glutathione S-transferase) sequences. Such fusion proteins can facilitate the purification of recombinant CRF2-12.

In another embodiment, the fusion protein is a CRF2-12-immunoglobulin fusion protein in which the CRF2-12 sequences comprising one or more domains are fused to sequences derived from a member of the immunoglobulin protein family.

The CFR2-12 fusion proteins (e.g., CRF2-12-immunoglobulin fusion proteins) of the invention can be incorporated into pharmaceutical compositions and administered to a subject to inhibit or augment an interaction between a cell surface receptor and its ligand. This could occur either by 1) binding to and removing available ligand for the receptor (Fc mediated scavenging of the ligand affecting bioavailability); 2) binding to the ligand and blocking its ability to bind to the cell receptor (antagonizing or neutralizing); 3) associating with another CRF member and thereby modulating (e.g., inhibiting) a downstream signal transduction cascade; 4) associating with either a ligand or another CRF and facilitating the activity of the ligand. By all of these mechanisms, a CRF2-12 protein may be used to modulate the interaction between a CRF2 receptor and its cognate ligand (e.g., an interaction between IL-10 and an IL-10 receptor and interaction between IL-22 and an IL-22 receptor).

Inhibition of the CRF2-12 ligand/CRF2-12 interaction can be used therapeutically for both the treatment of proliferative and differentiative disorders, e.g., cancer, modulating (e.g., promoting or inhibiting) cell survival as well as immunomodulatory disorders, autoimmunity, transplantation, and inflammation by alteration of cyotokine and chemokine cascade mechanisms. Moreover, the CRF2-12-immunoglobulin fusion proteins of the invention can be used as immunogens to produce anti-CRF2-12 antibodies in a subject, to purify CRF2-12 ligands, and in screening assays to identify molecules that inhibit the interaction of CRF2-12 with a CRF2-12 ligand.

A CRF2-12 chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A CRF2-12-encoding nucleic acid can be cloned into such an expression vector such that the fusion moiety is linked in-frame to the CRF2-12 protein.

Polypeptide Libraries

In addition, libraries of fragments of the CRF2-12 protein coding sequence can be used to generate a variegated population of CRF2-12 fragments for screening and subsequent selection of variants of a CRF2-12 protein. In one embodiment, a library of coding sequence fragments can be generated by treating a double stranded PCR fragment of a CRF2-12 coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the CRF2-12 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CRF2-12 proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify CRF2-12 variants (Arkin and Yourvan (1992) PNAS 89:7811–7815; Delgrave et al. (1993) Protein Engineering 6:327–331).

CRF2-12 Antibodies

Also included in the invention are antibodies to CRF2-12 proteins, or fragments of CRF2-12 proteins. The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, an antibody molecule obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated CRF2-12-related protein of the invention may be intended to serve as an antigen, or a portion or fragment thereof, and additionally can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, such as an amino acid sequence shown in SEQ ID NO:2, SEQ ID NO:4, SEQ ID NO:6, or SEQ ID NO:12, and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of CRF2-12-related protein that is located on the surface of the protein, e.g., a hydrophilic region. A hydrophobicity analysis of the human CRF2-12-related protein sequence will indicate which regions of a CRF2-12-related protein are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824–3828; Kyte and Doolittle 1982, *J. Mol. Biol.* 157: 105–142, each of which is incorporated herein by reference in its entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and Corynebacterium parvum, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25–28).

Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59–103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, Marcel Dekker, Inc., New York, (1987) pp. 51–63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980). Preferably, antibodies having a high degree of specificity and a high binding affinity for the target antigen are isolated.

After the desired hybridoma cells are identified, the clones can be subcloned by limiting dilution procedures and grown by standard methods. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, *Nature* 368 812–13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, $F_{ab}$, $F_{ab}'$, $F(ab')_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., *Nature*, 321:522–525 (1986); Riechlnann et al. *Nature*, 332:323–327 (1988); Verhoeyen et al., *Science*, 239:1534–1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, *Curr. Op. Struct. Biol.*, 2:593–596 (1992)).

Human Antibodies

Fully human antibodies relate to antibody molecules in which essentially the entire sequences of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77–96). Human monoclonal antibodies may be utilized in the practice of the present invention and may be produced by using human hybridomas (see Cote, et al., 1983. Proc Natl Acad Sci USA 80: 2026–2030) or by transforming human B-cells with Epstein Barr Virus in vitro (see Cole, et al., 1985 In: MONOCLONAL ANTIBODIES AND CANCER THERAPY, Alan R. Liss, Inc., pp. 77–96).

In addition, human antibodies can also be produced using additional techniques, including phage display libraries (Hoogenboom and Winter, *J. Mol. Biol.*, 227:381 (1991); Marks et al., *J. Mol. Biol.*, 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (*Bio/Technology* 10, 779–783 (1992)); Lonberg et al. (*Nature* 368 856–859 (1994)); Morrison (*Nature* 368, 812–13 (1994)); Fishwild et al, (*Nature Biotechnology* 14, 845–51 (1996)); Neuberger (*Nature Biotechnology* 14, 826 (1996)); and Lonberg and Huszar (*Intern. Rev. Immunol.* 3 65–93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

$F_{ab}$ Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275–1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, *Nature,* 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., 1991 *EMBO J.,* 10:3655–3659.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology* 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other $F_{ab}$'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., *J. Exp. Med.* 175:217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described For example, bispecific antibodies have been produced using leucine zippers. Kostelny et al., *J. Immunol.* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., J. Exp Med., 176: 1191–1195 (1992) and Shopes, J. Immunol., 148: 2918–2922 (1992). Homodimeric antibodies with enhanced anti-tumor activity can also be prepared using heterobifunctional cross-linkers as described in Wolff et al. Cancer Research, 53: 2560–2565 (1993). Alternatively, an antibody can be engineered that has dual Fc regions and can thereby have enhanced complement lysis and ADCC capabilities. See Stevenson et al., Anti-Cancer Drug Design, 3: 219–230 (1989).

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

CRF2-12 Recombinant Expression Vectors and Host Cells

Another aspect of the invention pertains to vectors, preferably expression vectors, containing a nucleic acid encoding a CRF2-12 protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e-g., polyadenylation signals). Such regulatory sequences are described, for example, in Goeddel, Gene Expression Technology: Methods in Enzymology 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., CRF2-12 proteins, mutant forms of CRF2-12 proteins, fusion proteins, etc.).

The recombinant expression vectors of the invention can be designed for expression of CRF2-12 proteins in prokaryotic or eukaryotic cells. For example, CRF2-12 proteins can be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, e.g., Gottesman. GENE EXPRESSION TECHNOLOGY: METHODS IN ENZYMOLOGY 185. Academic Press, San Diego. Calif. (1990) 119–128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111–2118). Such alteration of nucleic acid sequences of the invention can be carried out by standard DNA synthesis techniques.

In another embodiment, the CRF2-12 expression vector is a yeast expression vector. Examples of vectors for expression in yeast *Saccharomyces cerivisae* include pYepSec1 (Baldari, et al., 1987. *EMBO J.* 6: 229–234), pMFa (Kurjan and Herskowitz, 1982. *Cell* 30: 933–943), pJRY88 (Schultz et al., 1987. *Gene* 54: 113–123), pYES2 (Invitrogen Corporation, San Diego, Calif.), and picZ (InVitrogen Corp, San Diego, Calif.).

Alternatively, CRF2-12 can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156–2165) and the pVL series (Lucklow and Summers, 1989. *Virology* 170: 31–39).

In yet another embodiment, a nucleic acid of the invention is expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187–195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268–277), lymphoid-specific promoters (Calame and Eaton, 1988. *Adv. Immunol.* 43: 235–275), in particular promoters of T cell receptors (Winoto and Baltimore, 1989. *EMBO J.* 8: 729–733) and immunoglobulins (Banerji, et al., 1983. *Cell* 33: 729–740; Queen and Baltimore, 1983. *Cell* 33: 741–748), neuron-specific promoters (e.g., the neurofilament promoter; Byrne and Ruddle, 1989. *Proc. Natl. Acad. Sci. USA* 86: 5473–5477), pancreas-specific promoters (Edlund, et al., 1985. *Science* 230: 912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374–379) and the α-fetoprotein promoter (Campes and Tilghman, 1989. *Genes Dev.* 3: 537–546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to CRF2-12 mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," *Reviews-Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, CRF2-12 protein can be expressed in bacterial cells such as *E. coli*, insect cells, yeast or mammalian cells (such as human, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding CRF2-12 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) CRF2-12 protein. Accordingly, the invention further provides methods for producing CRF2-12 protein using the host cells of the invention. In one embodiment, the method comprises culturing the host cell of invention (into which a recombinant expression vector encoding CRF2-12 protein has been introduced) in a suitable medium such that CRF2-12 protein is produced. In another embodiment, the method further comprises isolating CRF2-12 protein from the medium or the host cell.

Transgenic CRF2-12 Animals

The host cells of the invention can also be used to produce non-human transgenic animals. For example, in one embodiment, a host cell of the invention is a fertilized oocyte or an embryonic stem cell into which CRF2-12 protein-coding sequences have been introduced. Such host cells can then be used to create non-human transgenic animals in which exogenous CRF2-12 sequences have been introduced into their genome or homologous recombinant animals in which endogenous CRF2-12 sequences have been altered. Such animals are useful for studying the function and/or activity of CRF2-12 protein and for identifying and/or evaluating modulators of CRF2-12 protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous CRF2-12 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing CRF2-12-encoding nucleic acid into the male pronuclei of a fertilized oocyte (e.g., by microinjection, retroviral infection) and allowing the oocyte to develop in a pseudopregnant female foster animal. Sequences including SEQ ID NO:1, SEQ ID NO:3, SEQ ID NO:5, or SEQ ID NO:11 can be introduced as a transgene into the genome of a non-human animal. Alternatively, a non-human homologue of the human CRF2-12 gene, such as a mouse CRF2-12 gene, can be isolated based on hybridization to the human CRF2-12 cDNA (described further supra) and used as a transgene. Intronic sequences and polyadenylation signals can also be included in the transgene to increase the efficiency of expression of the transgene. A tissue-specific regulatory sequence(s) can be operably-linked to the CRF2-12 transgene to direct expression of CRF2-12 protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan, 1986. In: MANIPULATING THE MOUSE EMBRYO, Cold Spring Harbor Laboratory Press. Cold Spring Harbor, N.Y. Similar methods are used for production of other transgenic animals. A transgenic founder animal can be identified based upon the presence of the CRF2-12 transgene in its genome and/or expression of CRF2-12 mRNA in tissues or cells of the animals. A transgenic founder animal can then be used to breed additional animals carrying the transgene. Moreover, transgenic animals carrying a transgene-encoding CRF2-12 protein can further be bred to other transgenic animals carrying other transgenes.

To create a homologous recombinant animal, a vector is prepared which contains at least a portion of a CRF2-12 gene into which a deletion, addition or substitution has been introduced to thereby alter, e.g., functionally disrupt, the CRF2-12 gene. The CRF2-12 gene can be a human gene (e.g., the DNA of SEQ ID NO:1, SEQ ID NO:3, SEQ ID NO:5, or SEQ ID NO:11), but more preferably, is a non-human homologue of a human CRF2-12 gene. For example, a mouse homologue of human CRF2-12 gene of SEQ ID NO:1, SEQ ID NO:3, SEQ ID NO:5, or SEQ ID NO:11 can be used to construct a homologous recombination vector suitable for altering an endogenous CRF2-12 gene in the mouse genome. In one embodiment, the vector is designed such that, upon homologous recombination, the endogenous CRF2-12 gene is functionally disrupted (i.e., no longer encodes a functional protein; also referred to as a "knock out" vector).

Alternatively, the vector can be designed such that, upon homologous recombination the endogenous CRF2-12 gene is mutated or otherwise altered but still encodes functional protein (e.g., the upstream regulatory region can be altered to thereby alter the expression of the endogenous CRF2-12 protein). In the homologous recombination vector, the altered portion of the CRF2-12 gene is flanked at its 5'- and 3'-termini by additional nucleic acid of the CRF2-12 gene to allow for homologous recombination to occur between the exogenous CRF2-12 gene carried by the vector and an endogenous CRF2-12 gene in an embryonic stem cell. The additional flanking CRF2-12 nucleic acid is of sufficient length for successful homologous recombination with the endogenous gene. Typically, several kilobases of flanking DNA (both at the 5'- and 3'-termini) are included in the vector. See, e.g. Thomas, et al., 1987. *Cell* 51: 503 for a description of homologous recombination vectors. The vector is ten introduced into an embryonic stem cell line (e.g. by electroporation) and cells in which the introduced CRF2-12 gene has homologously-recombined with the endogenous CRF2-12 gene are selected. See, e.g., Li, et al., 1992. *Cell* 69: 915.

The selected cells are then injected into a blastocyst of an animal (e.g., a mouse) to form aggregation chimeras. See, e.g., Bradley, 1987. In: TERATOCARCINOMAS AND EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described further in Bradley, 1991. *Curr. Opin. Biotechnol.* 2: 823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, See, e.g., Lakso, et al., 1992. *Proc. Natl. Acad. Sci. USA* 89: 6232–6236. Another example of a recombinase system is the FLP recombinase system of *Saccharomyces cerevisiae*. See, O'Gorman, et al., 1991. *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, et al., 1997. *Nature* 385: 810–813. In brief, a cell (e.g., a somatic cell) from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

Pharmaceutical Compositions

The CRF2-12 nucleic acid molecules, CRF2-12 proteins, and anti-CRF2-12 antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257: 286–288 (1982) via a disulfide-interchange reaction. A chemotherapeutic agent (such as Doxorubicin) is optionally contained within the liposome. See Gabizon et al., J. National Cancer Inst., 81 (19): 1484 (1989).

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a CRF2-12 protein or anti-CRF2-12 antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci. USA* 91: 3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington : The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York. If the antigenic protein is intracellular and whole antibodies are used as inhibitors, internalizing antibodies are preferred. However, liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., 1993 *Proc. Natl. Acad. Sci. USA*, 90: 7889–7893. The formulation herein can also contain more than one active compound as necessary for the particular indication being treated, preferably those with complementary activities that do not adversely affect each other. Alternatively or in addition, the composition can comprise an agent that enhances its function, such as, for example, a cytotoxic agent, cytokine, chemotherapeutic agent or growth-inhibitory agent. Such molecules are suitably present in combination in amounts that are effective for the purpose intended. The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The pharmaceutical compositions can be included in a container, pack, or dispenser together with instructions for administration.

Screening and Detection Methods

The isolated nucleic acid molecules of the invention can be used to express CRF2-12 protein (e.g., via a recombinant expression vector in a host cell in gene therapy applications), to detect CRF2-12 mRNA (e.g., in a biological sample) or a genetic lesion in a CRF2-12 gene, and to modulate CRF2-12 activity, as described further, below. In addition, the CRF2-12 proteins can be used to screen drugs or compounds that modulate the CRF2-12 protein activity or expression as well as to treat disorders characterized by insufficient or excessive production of CRF2-12 protein or production of CRF2-12 protein forms that have decreased or aberrant activity compared to CRF2-12 wild-type protein. In addition, the anti-CRF2-12 antibodies of the invention can be used to detect and isolate CRF2-12 proteins and modulate CRF2-12 activity. For example, CRF2-12 activity includes T-cell or NK cell growth and differentiation, antibody production, and tumor growth.

The invention further pertains to novel agents identified by the screening assays described herein and uses thereof for treatments as described, supra.

Screening Assays

The invention provides a method (also referred to herein as a "screening assay") for identifying modulators, i.e., candidate or test compounds or agents (e.g., peptides, peptidomimetics, small molecules or other drugs) that bind to CRF2-12 proteins or have a stimulatory or inhibitory effect on, e.g., CRF2-12 protein expression or CRF2-12 protein activity. The invention also includes compounds identified in the screening assays described herein.

In one embodiment, the invention provides assays for screening candidate or test compounds which bind to or modulate the activity of the membrane-bound form of a CRF2-12 protein or polypeptide or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. *Anticancer Drug Design* 12:145.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. *Proc. Natl. Acad. Sci. U.S.A.* 90: 6909; Erb, et al., 1994. *Proc. Natl. Acad. Sci. USA*. 91: 11422; Zuckermann, et al., 1994. *J. Med. Chem.* 37: 2678; Cho, et al., 1993. *Science* 261: 1303; Carrell, et al., 1994. *Angew. Chem. Int. Ed. Engl.* 33: 2059; Carell, et al., 1994. *Angew. Chem. Int. Ed. Engl.* 33: 2061; and Gallop, et al., 1994. *J. Med. Chem.* 37: 1233.

Libraries of compounds may be presented in solution (e.g., Houghten, 1992. *Biotechniques* 13: 412–421), or on beads (Lam, 1991. *Nature* 354: 82–84), on chips (Fodor, 1993. *Nature* 364: 555–556), bacteria (Ladner, U.S. Pat. No. 5,223,409), spores (Ladner, U.S. Pat. 5,233,409), plasmids (Cull, et al., 1992. *Proc. Natl. Acad. Sci. USA* 89:1865–1869) or on phage (Scott and Smith, 1990. *Science* 249: 386–390; Devlin, 1990. *Science* 249: 404–406; Cwirla, et al., 1990. *Proc. Natl. Acad. Sci. U.S.A.* 87: 6378–6382; Felici, 1991. *J. Mol. Biol.* 222: 301–310; Ladner, U.S. Pat. No. 5,233,409.).

In one embodiment, an assay is a cell-based assay in which a cell which expresses a membrane-bound form of CRF2-12 protein, or a biologically-active portion thereof, on the cell surface is contacted with a test compound and the ability of the test compound to bind to a CRF2-12 protein determined. The cell, for example, can be of mammalian origin or a yeast cell. Determining the ability of the test compound to bind to the CRF2-12 protein can be accomplished, for example, by coupling the test compound with a radioisotope or enzymatic label such that binding of the test compound to the CRF2-12 protein or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of CRF2-12 protein, or a biologically-active portion thereof, on the cell surface with a known compound which binds CRF2-12 to form an assay mixture, contacting the assay mixture with a test compound, and determining the ability of the test compound to interact with a CRF2-12 protein, wherein determining the ability of the test compound to interact with a CRF2-12 protein comprises determining the ability of the test compound to preferentially bind to CRF2-12 protein or a biologically-active portion thereof as compared to the known compound.

In another embodiment, an assay is a cell-based assay comprising contacting a cell expressing a membrane-bound form of CRF2-12 protein, or a biologically-active portion thereof, on the cell surface with a test compound and determining the ability of the test compound to modulate (e.g., stimulate or inhibit) the activity of the CRF2-12 protein or biologically-active portion thereof. Determining the ability of the test compound to modulate the activity of CRF2-12 or a biologically-active portion thereof can be accomplished, for example, by determining the ability of the CRF2-12 protein to bind to or interact with a CRF2-12 target molecule. As used herein, a "target molecule" is a molecule with which a CRF2-12 protein binds or interacts in nature, for example, a molecule on the surface of a cell which expresses a CRF2-12 interacting protein, a molecule on the surface of a second cell, a molecule in the extracellular milieu, a molecule associated with the internal surface of a cell membrane or a cytoplasmic molecule. A CRF2-12 target molecule can be a non-CRF2-12 molecule or a CRF2-12 protein or polypeptide of the invention In one embodiment, a CRF2-12 target molecule is a component of a signal transduction pathway that facilitates transduction of an extracellular signal (e.g. a signal generated by binding of a compound to a membrane-bound CRF2-12 molecule) through the cell membrane and into the cell. The target, for example, can be a second intercellular protein that has catalytic activity or a protein that facilitates the association of downstream signaling molecules with CRF2-12.

Determining the ability of the CRF2-12 protein to bind to or interact with a CRF2-12 target molecule can be accomplished by one of the methods described above for determining direct binding. In one embodiment, determining the ability of the CRF2-12 protein to bind to or interact with a CRF2-12 target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a CRF2-12-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting a CRF2-12 protein or biologically-active portion thereof with a test compound and determining the ability of the test compound to bind to the CRF2-12 protein or biologically-active portion thereof. Binding of the test compound to the CRF2-12 protein can be determined either directly or indirectly as described above. In one such embodiment, the assay comprises contacting the CRF2-12 protein or biologically-active portion thereof with a known compound which binds CRF2-12 to form an assay mixture, contacting the assay mixture with a test compound, and determining the ability of the test compound to interact with a CRF2-12 protein, wherein determining the ability of the test compound to interact with a CRF2-12 protein comprises determining the ability of the test compound to preferentially bind to CRF2-12 or biologically-active portion thereof as compared to the known compound.

In still another embodiment, an assay is a cell-free assay comprising contacting CRF2-12 protein or biologically-active portion thereof with a test compound and determining the ability of the test compound to modulate (e.g. stimulate or inhibit) the activity of the CRF2-12 protein or biologically-active portion thereof. Determining the ability of the test compound to modulate the activity of CRF2-12 can be accomplished, for example, by determining the ability of the CRF2-12 protein to bind to a CRF2-12 target molecule by one of the methods described above for determining direct binding. In an alternative embodiment, determining the ability of the test compound to modulate the activity of CRF2-12 protein can be accomplished by determining the ability of the CRF2-12 protein further modulate a CRF2-12 target molecule. For example, the catalytic/enzymatic activity of the target molecule on an appropriate substrate can be determined as described above.

In yet another embodiment, the cell-free assay comprises contacting the CRF2-12 protein or biologically-active portion thereof with a known compound which binds CRF2-12 protein to form an assay mixture, contacting the assay mixture with a test compound, and determining the ability of the test compound to interact with a CRF2-12 protein wherein determining the ability of the test compound to interact with a CRF2-12 protein comprises determining the ability of the CRF2-12 protein to preferentially bind to or modulate the activity of a CRF2-12 target molecule.

The cell-free assays of the invention are amenable to use of both the soluble form or the membrane-bound form of CRF2-12 protein. In the case of cell-free assays comprising the membrane-bound form of CRF2-12 protein, it may be desirable to utilize a solubilizing agent such that the membrane-bound form of CRF2-12 protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment of the above assay methods of the invention, it may be desirable to immobilize either CRF2-12 protein or its target molecule to facilitate separation of complexed from uncomplexed forms of one or both of the proteins, as well as to accommodate automation of the assay. Binding of a test compound to CRF2-12 protein, or interaction of CRF2-12 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-CRF2-12 fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or CRF2-12 protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of CRF2-12 protein binding or activity determined using standard techniques.

Other techniques for immobilizing proteins on matrices can also be used in the screening assays of the invention. For example, either the CRF2-12 protein or its target molecule can be immobilized utilizing conjugation of biotin and streptavidin. Biotinylated CRF2-12 protein or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with CRF2-12 protein or target molecules, but which do not interfere with binding of the CRF2-12 protein to its target molecule, can be derivatized to the wells of the plate, and unbound target or CRF2-12 protein trapped in the wells by antibody conjugation. Methods for detecting such complexes, in addition to those described above for the GST-immobilized complexes, include immunodetection of complexes using antibodies reactive with the CRF2-12 protein or target molecule, as well as enzyme-linked assays that rely on detecting an enzymatic activity associated with the CRF2-12 protein or target molecule.

In another embodiment, modulators of CRF2-12 protein expression are identified in a method wherein a cell is contacted with a candidate compound and the expression of CRF2-12 mRNA or protein in the cell is determined. The level of expression of CRF2-12 mRNA or protein in the presence of the candidate compound is compared to the level of expression of CRF2-12 mRNA or protein in the absence of the candidate compound. The candidate compound can then be identified as a modulator of CRF2-12 mRNA or protein expression based upon this comparison. For example, when expression of CRF2-12 mRNA or protein is greater (i.e., statistically significantly greater) in the presence of the candidate compound than in its absence, the candidate compound is identified as a stimulator of CRF2-12 mRNA or protein expression. Alternatively, when expression of CRF2-12 mRNA or protein is less (statistically significantly less) in the presence of the candidate compound than in its absence, the candidate compound is identified as an inhibitor of CRF2-12 mRNA or protein expression. The level of CRF2-12 mRNA or protein expression in the cells can be determined by methods described herein for detecting CRF2-12 mRNA or protein.

In yet another aspect of the invention, the CRF2-12 proteins can be used as "bait proteins" in a two-hybrid assay or three hybrid assay (see. e.g., U.S. Pat. No. 5,283,317; Zervos, et al., 1993. *Cell* 72: 223–232; Madura, et al., 1993. *J. Biol. Chem.* 268: 12046–12054; Bartel, et al., 1993. *Biotechniques* 14: 920–924; Iwabuchi, et al., 1993. *Oncogene* 8: 1693–1696; and Brent WO 94/10300), to identify other proteins that bind to or interact with CRF2-12 ("CRF2-12-binding proteins" or "CRF2-12-bp") and modulate CRF2-12 activity. Such CRF2-binding proteins are also likely to be involved in the propagation of signals by the CRF2-12 proteins as, for example, upstream or downstream elements of the CRF2-12 pathway.

The two-hybrid system is based on the modular nature of most transcription factors, which consist of separable DNA-binding and activation domains. Briefly, the assay utilizes two different DNA constructs. In one construct, the gene that codes for CRF2-12 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a CRF2-12-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with CRF2-12.

The invention further pertains to novel agents identified by the aforementioned screening assays and uses thereof for treatments as described herein.

The invention will be further illustrated in the following non-limiting examples.

EXAMPLE 1

Isolation of Murine CRF2-12 Sequences

Murine genomic and EST DNA databases were screened and certain clones were identified as containing homology to hCRF2-12. Based on this homology, the murine sequences containing sequences encoding the amino and carboxy terminal CRF-2-12 sequences were defined. Primers corresponding to the ends 5' and 3' ends of the ORF -ms15-6 (GGAACTCTGGTTGCCAGACAAGCACAC) (SEQ ID NO:38) and primer ms53-5 (reverse complement of CAAGGAGAGATGTGTGCAGATTCCATGA) (SEQ ID NO:39), respectively, were synthesized and used as primers in a PCR reaction. DNA products from these PCR reactions were cloned into pCRII TOPO vector by TA cloning and the plasmids were sequenced.

EXAMPLE 2

Identification of Regions of Homology between Human and Murine CRF2-12 Polypeptide Sequences The amino acid sequences of human CRF2-12 (SEQ ID NO:34) and munne CRF2-12 (SEQ ID NO:35) polypeptides were compared. The alignment is presented below. Alignments were prepared as described in Henikoff et al., *Proc. Natl. Acad. Sci.* (USA) 89:10915–19, 1992. For the alignment shown, gap weight=8, average match=2.912, length weight=2, average mismatch=-2.003, quality=829, length=1101, ratio=3.589, gaps=1. The two proteins were found to be 69.565% similar and 66.957% identical.

```
 832  LcaaGlnQuuaLeuLSerSMMPKHCLLGLLI.ILLSSATEIQPARVSLTP   880
                         ||||||  ||  ||  |.         |    |||
   1  ....................MMPKHCFLGFLISFFLTGVAGTQSTHESLKP   31

881  QKVRFQSRNFHNILHWQAGSSLPSNNSIYFVQYKMYGQSQWEDKVDCWGT   930
      |:|.||||||||| ||  .|  .|.|:|||||.||| ||..| |||||
  32  QRVQFQSRNFHNILQWQPGRALTGNSSVYFVQYKIYGQRQWKNKEDCWGT   81

931  TALFCDLTNETLDPYELYYGRVMTACAGRHSAWTRTPRFTPWWETKLDPP   880
      |  ||||.||  |   ||||||   :| |. ||||||||||||| ||
  82  QELSCDLTSETSDIQEPYYGRVRAASAGSYSEWSMTPRFTPWWETKIDPP   131

981  VVTITRVNASLRVLLRPPELPNRNQSGKNASMETYYGLVYRVFTINNSLE   1030
      |. ||.||  || :|   |  |   || |.|| |.|||| ||||||||
 132  VMNITQVNGSLLVILHAPNLPYRYQKEKNVSIEDYYELLYRVFIINNSLE   181

1031  KEQKAYEGTQRAVEIEGLIPHSSYCVVAEMYQPMFDRRSPRSKERCVQIP   1080
      ||||  |||   ||||||| | |||||||||||.|||| |||.|||:|
 182  KEQKVYEGAHRAVEIEALTPHSSYCVVAEIYQPMLDRRSQRSEERCVEIP   231
```

The alignment reveals that the two proteins are 69.565% similar and 66.957% identical. Complete or nearly complete identity is detected for some regions of the two polypeptides, e.g., over polypeptide regions including the amino acids MMPKHCL/FLG L/FLI, (SEQ ID NO:13), FQSRNFH-NILH/QWQ A/PG (SEQ ID NO:14), SI/VYFVQYKM/IYGQS/RQW (SEQ ID NO:15), TPRFTPWWETKL/ID-PPV (SEQ ID NO. 16). LV/LYRVFT/IINNSLEKEQKA/VYEG (SEQ ID NO:17), RAVEIEG/ALI/TPHSSYCVVALE/IYQPM (SEQ ID NO:18), and DRRSP/QRSK/EERCVQ/EIP (SEQ ID NO:19).

EXAMPLE 3

Tissue Expression Pattern of CRF2-12 RNA Sequences

Expression of CRF2-12 sequences was examined using an Origene kit containing a panel of first strand cDNA sequences. Primers specific for hCRF2-12 sequences were used to probe RNA from a variety of tissues for the presence of CRF2-12 sequences. Relative expression levels were assigned using a "+" or "−" scoring system, with "−" denoting no RNA sequences detected and "++++" denoting high expression. Lower relative levels of CRF2-12 RNA sequences were assigned potential scores of "+", "++", or "+++".

High levels (++++) of CRF2-12 transcripts were detected in placental and skin tissue. Low to moderate levels of CRF2-12 transcripts were detected in colon (+), prostate (+), small intestine (++), and spleen (++). No to low levels of CRF2-12 transcripts were detected in brain, kidney, liver, muscle, stomach, testes, thyroid, adrenal, pancreas, ovary, uterus, peripheral blood lymphocytes (PBL), bone marrow, fetal brain, and fetal liver (all (−)); and heart or salivary tissue (both (+/−)).

These results demonstrate that probes that recognize CRF2-12 nucleic acids and/or polypeptides are useful for detecting tissues in which CRF2-12 sequences are highly expressed, e.g., placental and skin tissue. Such probes can also be used to detect colon, prostate, small intestine, and spleen tissue. Absence of hybridization to probes that recognize CRF2-12 nucleic acids and/or polypeptides can also be used to verify the identity of tissues in which CRF2-12 is not expressed, e.g., stomach, testes, thyroid, adrenal, pancreas, ovary, uterus, peripheral blood lymphocytes (PBL), bone marrow, fetal brain, and fetal liver tissues.

EXAMPLE 4

Construction of Vectors Including CRF2-12 Nucleic Acid Sequences

A murine CRF2-12 (mCRF2-112) cDNA was isolated as a Not 1-HindIII restriction enzyme fragment from a TOPO vector. The fragment was subcloned into HindIII and NotI digested adenovirus vector Adore 1-2. The construct was verified by restriction digestion analysis and sequencing of the cDNA insert. In this vector, mCRF2-12 is under the control of the cytomegalovirus (CMV) immediate early promoter and enhancer.

The construct is used to construct a replication-defective, E1/E3 deleted recombinant, type 5 (d1327) adenovirus by homologous recombination in human embryonic kidney 293 cells (ATCC, Rockville, Md.).

EXAMPLE 5

Construction of a Fusion Protein Including a CRF2-12 Polypeptide Sequences

A fusion protein including CRF-2-12 polypeptide sequences is constructed from a fusion gene corresponding to all of the mCRF2-12 ORF fused to a mutated mouse IgG2a Fc domain. Primers are designed and used to amplify in a PCR reaction mCRF2-12 from the TOPO vector using a blunt-end PCR polymerase.

A fusion gene corresponding to all of the mCRF2-12 ORF fused to a mutated mouse IgG2a Fc domain is constructed using primers that PCR amplify mCRF2-12 from the TOPO vector using a blunt-end PCR polymerase. The 5' primer (VL334: GAATTCGTCGACCCACCATGCCTAAG-CATTGCCTTC (SEQ ID NO:31) incorporates a SalI site and Kozak leader sequence upstream of mCRF2-12 sequence. The 3' primer is VL335: TGGAATCTGCACA-CATCTCTCC (SEQ ID NO:32). The PCR product was cut with SalI and ligated to a SalI and blunt FspI cut Gateway entry vector, pG352, that fused the PCR amplified mCRF2-12 in-frame to the hinge, CH2 and CH3 region sequences of a mutated IgG2a gene. The resulting transformation is a plasmid that contains an in-frame fusion of mCRF2-12 to mIgG2a hinge —CH2—CH3. This fusion entry vector was then used to shuttle the insert into a retroviral Gateway destination vector, pG343. Cell lines are made that make and amplify retrovirus encoding a mCRF-12-FcG2am fusion gene.

The resulting construct is a plasmid that contains an in-frame fusion of mCRF2-12 to mIgG2a hinge —CH2—CH3. This fusion entry vector is then used to shuttle the insert into a retroviral Gateway destination vector pG343. Cell lines are constructed that make and amplify retrovirus encoding a mCRF-12-FcG2am fusion gene. This virus is used to transduce cells that are used in animal models of disease and that incorporate the adoptive transfer of these cells.

EXAMPLE 6

Detection of a Placental Tissue Using CRF2-12 Nucleic Acid Sequence Probes

A biological sample suspected of containing placental tissue is provided and RNA is recovered. The RNA is contacted with a probe that specifically detects CRF2-12 RNA samples Presence of CRF2-12 RNA indicates the sample contains placental tissue.

EXAMPLE 7

Detection of Skin Tissue Using CRF2-12 Nucleic Acid Sequence Probes

A biological sample suspected of containing skin tissue is provided and RNA is recovered. The RNA is contacted with a probe that specifically detects CRF2-12 RNA samples Presence of CRF2-12 RNA in the sample indicates the sample contains skin tissue.

EXAMPLE 8

Detection of a Placental Tissue Using Probes that Specifically Detect CRF2-12 Polypeptides A biological sample suspected of containing placental tissue is provided and protein is recovered. The protein is contacted with an antibody probe that specifically binds a CRF2-12 polypeptide. Presence of CRF2-12 polypeptide in the sample indicates the sample contains placental tissue.

EXAMPLE 9

Detection of Skin Tissue Using Probes that Specifically Detect CRF2-12 Polypeptides A biological sample suspected of containing skin tissue is provided and protein is recovered. The protein is contacted with an antibody probe that specifically binds a CRF2-12 polypeptide. Presence of CRF2-12 polypeptide in the sample indicates the sample contains skin tissue.

EXAMPLE 10

A Sequence Variant of the Disclosed CRF2-12 Polypeptide Amino Acid Sequence (SEQ ID NO:2)

A polypeptide sequence differing by one amino acid sequence from the amino acid sequence of SEQ ID NO:2 is shown in SEQ ID NO:20. The variant amino acid sequence is shown in bold-font. A glutamine at position 23 in the polypeptide sequence shown in SEQ ID NO:2 is replaced with an asparagine in the corresponding position in SEQ ID NO:20.

(SEQ ID NO:20)

```
MMPKHCFLGFLISFFLTGVAGTNSTHESLKPQRVQFQSRNFHNILQWQPGRALTGNSSVYFVQYKIYGQRQWKNKEDC

WGTQELSCDLTSETSDIQEPYYGRVRAASAGSYSEWSMTPRFTPWWETKIDPPVMNITQVNGSLLVILHAPNLPYRYQ

KEKNVSIEDYYELLYRVFIINNSLEKEQKVYEGAHRAVEIEALTPHSSYCVVAEIYQPMLDRRSQRSEERCVEIP
```

EXAMPLE 11

A Sequence Variant of the Disclosed CRF2-12 Polypeptide Amino Acid Sequence (SEQ ID NO:2)

A polypeptide sequence differing by one amino acid sequence from the amino acid sequence of SEQ ID NO:2 is shown in SEQ ID NO:21. The variant amino acid sequence is shown in bold-font. A histidine at position 26 in the polypeptide sequence shown in SEQ ID NO:2 is replaced with an arginine in the corresponding position in SEQ ID NO:21.

(SEQ ID NO:21)

```
MMPKHCFLGFLISFFLTGVAGTQSTRESLKPQRVQFQSRNFHNILQWQPGRALTGNSSVYFVQYKIYGQRQWKNKEDC

WGTQELSCDLTSETSDIQEPYYGRVRAASAGSYSEWSMTPRFTPWWETKIDPPVMNITQVNGSLLVILHAPNLPYRYQ

KEKNVSIEDYYELLYRVFIINNSLEKEQKVYEGAHRAVEIEALTPHSSYCVVAEIYQPMLDRRSQRSEERCVEIP
```

EXAMPLE 12

A Sequence Variant of the Disclosed CRF2-12 Polypeptide Amino Acid Sequence (SEQ ID NO:2)

A polypeptide sequence differing by one amino acid sequence from the amino acid sequence of SEQ ID NO:2 is shown in SEQ ID NO:22. The variant amino acid sequence is shown in bold-font. A glutamic acid at position 27 in the polypeptide sequence shown in SEQ ID NO:2 is replaced with an aspartic acid in the corresponding position in SEQ ID NO:22.

(SEQ ID NO:22)
MMPKHCFLGFLISFFLTGVAGTQSTHDSLKPQRVQFQSRNFHNILQWQPGRALTGNSSVYFVQYKIYGQRQWKNKEDC

WGTQELSCDLTSETSDIQEPYYGRVRAASAGSYSEWSMTPRFTPWWETKIDPPVMNITQVNGSLLVILHAPNLPYRYQ

KEKNVSIEDYYELLYRVFIINNSLEKEQKVYEGAHRAVEIEALTPHSSYCVVAEIYQPMLDRRSQRSEERCVEIP

EXAMPLE 13

A Sequence Variant of the Disclosed CRF2-12 Polypeptide Amino Acid Sequence (SEQ ID NO:2)

A polypeptide sequence differing by one amino acid sequence from the amino acid sequence of SEQ ID NO:2 is shown in SEQ ID NO:23. The variant amino acid sequence is shown in bold-font. A leucine at position 29 in the polypeptide sequence shown in SEQ ID NO:2 is replaced with a valine in the corresponding position in SEQ ID NO:23.

(SEQ ID NO:23)
MMPKHCFLGFLISFFLTGVAGTQSTHESVKPQRVQFQSRNFHNILQWQPGRALTGNSSVYFVQYKIYGQRQWKNKEDC

WGTQELSCDLTSETSDIQEPYYGRVRAASAGSYSEWSMTPRFTPWWETKIDPPVMNITQVNGSLLVILHAPNLPYRYQ

KEKNVSIEDYYELLYRVFIINNSLEKEQKVYEGAHRAVEIEALTPHSSYCVVAEIYQPMLDRRSQRSEERCVEIP

EXAMPLE 14

A Sequence Variant of the Disclosed CRF2-12 Polypeptide Amino Acid Sequence (SEQ ID NO:2)

A polypeptide sequence differing by one amino acid sequence from the amino acid sequence of SEQ ID NO:2 is shown in SEQ ID NO:24. The variant amino acid sequence is shown in bold-font. A lysine at position 30 in the polypeptide sequence shown in SEQ ID NO:2 is replaced with a histidine in the corresponding position in SEQ ID NO:24.

(SEQ ID NO:24)
MMPKHCFLGFLISFFLTGVAgTQSTHESLHPQRVQFQSRNFHNILQWQPGRALTGNSSVYFVQYKIYGQRQWKNKEDC wGTQELSCDLTSETSDIQEPYYGRVRAASAGSYSEWSMTPRFTPWWETKIDPPVMNITQVNGSLLVILHAPNLPYRYQ

KEKNVSIEDYYELLYRVFIINNSLEKEQKVYEGAHRAVEIEALTPHSSYCVVAEIYQPMLDRRSQRSEERCVEIP

EXAMPLE 15

A Sequence Variant of the Disclosed CRF2-12 Polypeptide Amino Acid Sequence (SEQ ID NO:2)

A polypeptide sequence differing by one amino acid sequence from the amino acid sequence of SEQ ID NO:2 is shown in SEQ ID NO:25. The variant amino acid sequence is shown in bold-font. An arginine at position 33 in the polypeptide sequence shown in SEQ ID NO:2 is replaced with a lysine in the corresponding position in SEQ ID NO:25.

(SEQ ID NO:25)
MMPKHCFLGFLISFFLTGVAGTQSTHESLKPQKVQFQSRNFHNILQWQPGRALTGNSSVYFVQYKIYGQRQWKNKEDC

WGTQELSCDLTSETSDIQEPYYGRVRAASAGSYSEWSMTPRFTPWWETKIDPPVMNITQVNGSLLVILHAPNLPYRYQ

KEKNVSIEDYYELLYRVFIINNSLEKEQKVYEGAHRAVEIEALTPHSSYCVVAEIYQPMLDRRSQRSEERCVEIP

EXAMPLE 16

A Sequence Variant of the Disclosed CRF2-12 Polypeptide Amino Acid Sequence (SEQ ID NO:2)

A polypeptide sequence differing by one amino acid sequence from the amino acid sequence of SEQ ID NO:2 is shown in SEQ ID NO:26. The variant amino acid sequence is shown in bold-font. An asparagine at position 40 in the polypeptide sequence shown in SEQ ID NO:2 is replaced with a glutamine in the corresponding position in SEQ ID NO:26.

(SEQ ID NO:26)
MMPKHCFLGFLISFFLTGVAGTQSTHESLKPQRVQFQSRQFHNILQWQPGRALTGNSSVYFVQYKIYGQRQWKNKEDC

WGTQELSCDLTSETSDIQEPYYGRVRAASAGSYSEWSMTPRFTPWWETKIDPPVMNITQVNGSLLVILHAPNLPYRYQ

KEKNVSIEDYYELLYRVFIINNSLEKEQKVYEGAHRAVEIEALTPHSSYCVVAEIYQPMLDRRSQRSEERCVEIP

EXAMPLE 17

A Sequence Variant of the Disclosed CRF2-12 Polypeptide Amino Acid Sequence (SEQ ID NO:2)

A polypeptide sequence differing by one amino acid sequence from the amino acid sequence of SEQ ID NO:2 is shown in SEQ ID NO:27. The variant amino acid sequence is shown in bold-font. A leucine at position 45 in the polypeptide sequence shown in SEQ ID NO:2 is replaced with a valine in the corresponding position in SEQ ID NO:27.

(SEQ ID NO:27)
MMPKHCFLGFLISFFLTGVAGTQSTHESLKPQRVQFQSRNFHNIVQWQPGPALTGNSSVYFVQYKIYGQRQWKNKEDC

WGTQELSCDLTSETSDIQEPYYGRVRAASAGSYSEWSMTPRFTPWWETKIDPPVMNITQVNGSLLVILHAPNLPYRYQ

KEKNVSIEDYYELLYRVFIINNSLEKEQKVYEGAHRAVEIEALTPHSSYCVVAEIYQPMLDRRSQRSEERCVEIP

EXAMPLE 18

A Sequence Variant of the Disclosed CRF2-12 Polypeptide Amino Acid Sequence (SEQ ID NO:2)

A polypeptide sequence differing by one amino acid sequence from the amino acid sequence of SEQ ID NO:2 is shown in SEQ ID NO:28. The variant amino acid sequence is shown in bold-font. An alanine at position 52 in the polypeptide sequence shown in SEQ ID NO:2 is replaced with a leucine in the corresponding position in SEQ ID NO:28.

(SEQ ID NO:28)

MMPKHCFLGFLISFFLTGVAgTQSTHESLKPQRVQFQSRNFHNILQWQPGRLLTGNSSVYFVQYKIYGQRQWKNKEDC
WGTQELSCDLTSETSDIQEPYYGRVRAASAGSYSEWSMTPRFTPWWETKIDPPVMNITQVNGSLLVILHAPNLPYRYQ
KEKNVSIEDYYELLYRVFIINNSLEKEQKVYEGAHRAVEIEALTPHSSYCVVAEIYQPMLDRRSQRSEERCVEIP

EXAMPLE 19

A Sequence Variant of the Disclosed CRF2-12 Polypeptide Amino Acid Sequence (SEQ ID NO:2)

A polypeptide sequence differing by one amino acid sequence from the amino acid sequence of SEQ ID NO:2 is shown in SEQ ID NO:29. The variant amino acid sequence is shown in bold-font. A leucine at position 53 in the polypeptide sequence shown in SEQ ID NO:2 is replaced with an alanine in the corresponding position in SEQ ID NO:29.

(SEQ ID NO:29)

MMPKHCFLGFLISFFLTGVAGTQSTHESLKPQRVQFQSRNFHNILQWQPGRAATGNSSVYFVQYKIYGQRQWKNKEDC

WGTQELSCDLTSETSDIQEPYYGRVRAASAGSYSEWSMTPRFTPWWETKIDPPVMNITQVNGSLLVILHAPNLPYRYQ

KEKNVSIEDYYELLYRVFIINNSLEKEQKVYEGAHRAVEIEALTPHSSYCVVAEIYQPMLDRRSQRSEERCVEIP

EXAMPLE 20

A Sequence Variant of the Disclosed CRF2-12 Polypeptide Amino Acid Sequence (SEQ ID NO:2)

A polypeptide sequence differing by one amino acid sequence from the amino acid sequence of SEQ ID NO:2 is shown in SEQ ID NO:30. The variant amino acid sequence is shown in bold-font. A valine at position 59 in the polypeptide sequence shown in SEQ ID NO:2 is replaced with an isoleucine in the corresponding position in SEQ ID NO:30.

(SEQ ID NO:30)

MMPKHCFLGFLISFFLTGVAGTQSTHESLKPQRVQFQSRNFHNILQWQPGRALTGNSSIYFVQYKIYGQRQWKNKEDC

WGTQELSCDLTSETSDIQEPYYGRVRAASAGSYSEWSMTPRFTPWWETKIDPPVMNITQVNGSLLVILHAPNLPYRYQ

KEKNVSIEDYYELLYRVFIINNSLEKEQKVYEGAHRAVEIEALTPHSSYCVVAEIYQPMLDRRSQRSEERCVEIP

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A substantially purified polypeptide comprising an amino acid sequence at least 95% identical to SEQ ID NO:4, provided said polypeptide comprises amino acids 67–98 of SEQ ID NO:4, and wherein said polypeptide binds IL-10 or IL-22.

2. The polypeptide of claim 1, wherein said polypeptide comprises the amino acid sequence of SEQ ID NO:4.

3. A fusion protein comprising the polypeptide of claim 1.

4. The fusion protein of claim 3, wherein said fusion protein comprises at least one member selected from the group consisting of an Fc region of an immunoglobulin molecule, a FLAG epitope, a HIS tag, and a MYC tag.

5. The polypeptide of claim 1, wherein said polypeptide comprises at least one polypeptide sequence selected from the group consisting of,

| | |
|---|---|
| MMPKHCL/FLGL/FLI, | (SEQ ID NO:13), |
| FQSRNFHNILH/QWQA/PG | (SEQ ID NO:14), |
| SI/VYFVQYKM/IYGQS/RQW | (SEQ ID NO:15), |
| TPRFTPWWETKL/IDPPV | (SEQ ID NO:16), |
| LV/LYRVFT/IINNSLEKEQKA/VYEG | (SEQ ID NO:17), |

-continued

RAVEIEG/ALI/TPHSSYCVVAEM/IYQPM (SEQ ID NO:18), and

DRRSP/QRSK/EERCVQ/EIP (SEQ ID NO:19).

6. The polypeptide of claim 1, wherein the amino acid sequence of said polypeptide is at least 98% identical to SEQ ID NO:4.

7. The polypeptide of claim 1, wherein the amino acid sequence of said polypeptide is at least 99% identical to SEQ ID NO:4.

8. The polypeptide of claim 1, wherein said polypeptide binds IL-10.

9. The polypeptide of claim 1, wherein said polypeptide binds IL-22.

10. A pharmaceutical composition comprising the polypeptide of claim 1 and a pharmaceutically acceptable carrier.

11. A kit comprising in one or more containers the polypeptide of claim 1.

* * * * *